(12) United States Patent
Hunt et al.

(10) Patent No.: US 11,791,030 B2
(45) Date of Patent: Oct. 17, 2023

(54) WOUND ANALYSIS DEVICE AND METHOD

(71) Applicant: Smith & Nephew PLC, Watford (GB)

(72) Inventors: Allan Kenneth Frazer Grugeon Hunt, East Riding of Yorkshire (GB); Marcus Damian Phillips, Wakefield (GB)

(73) Assignee: Smith & Nephew PLC, Watford (GB)

( * ) Notice: Subject to any disclaimer, the term of this patent is extended or adjusted under 35 U.S.C. 154(b) by 333 days.

(21) Appl. No.: 16/613,782

(22) PCT Filed: May 11, 2018

(86) PCT No.: PCT/EP2018/062206
§ 371 (c)(1),
(2) Date: Nov. 14, 2019

(87) PCT Pub. No.: WO2018/210692
PCT Pub. Date: Nov. 22, 2018

(65) Prior Publication Data
US 2021/0145359 A1    May 20, 2021

Related U.S. Application Data

(60) Provisional application No. 62/506,551, filed on May 15, 2017.

(51) Int. Cl.
*A61B 5/00*    (2006.01)
*A61B 5/0522*    (2021.01)
(Continued)

(52) U.S. Cl.
CPC ........... *G16H 20/30* (2018.01); *A61B 5/0022* (2013.01); *A61B 5/0077* (2013.01);
(Continued)

(58) Field of Classification Search
CPC ..... A61B 5/7455; A61B 5/746; A61B 5/7405; A61B 5/74; A61B 5/0522; A61B 5/0082;
(Continued)

(56) References Cited

U.S. PATENT DOCUMENTS 3,896,802 A   7/1975  Williams
4,334,530 A   6/1982  Hassell
(Continued)

FOREIGN PATENT DOCUMENTS

CN    105232229    1/2016
CN    105395184    3/2016
(Continued)

OTHER PUBLICATIONS

Heinrich et al. (WO 03/105689) (Machine English translation from ESPACE.net) (Year: 2003).*
(Continued)

*Primary Examiner* — David J. McCrosky
*Assistant Examiner* — Nidhi N Patel
(74) *Attorney, Agent, or Firm* — Knobbe, Martens, Olson & Bear, LLP

(57) ABSTRACT

Embodiments of tissue monitoring and therapy systems and methods are disclosed. In some embodiments, a monitoring and therapy system comprises collecting video images of a tissue site, amplifying said video images via Eulerian Video Magnification, and determining a treatment parameter from the amplified video images detectable by Eulerian Video Magnification. If the treatment parameter differs from a threshold, an alert may be generated.

14 Claims, 11 Drawing Sheets

(51) Int. Cl.
*G16H 20/30* (2018.01)
*A61M 1/00* (2006.01)

(52) U.S. Cl.
CPC .......... *A61B 5/0522* (2013.01); *A61B 5/4836* (2013.01); *A61B 5/7405* (2013.01); *A61B 5/746* (2013.01); *A61M 1/915* (2021.05); *A61M 1/916* (2021.05); *A61M 1/985* (2021.05)

(58) Field of Classification Search
CPC ..... A61B 5/0077; A61B 5/002; A61B 5/0022; A61B 5/4833; A61B 5/4839; A61B 5/4836; A61B 5/6802; A61B 5/0075; A61B 5/01; A61B 5/024; A61B 5/0261; A61B 5/445; A61B 5/447; A61B 5/4869; A61B 8/5223; A61B 2090/065; A61B 2505/50; A61B 2576/00; G16H 20/30; G16H 20/40; G16H 30/40; A61M 1/915; A61M 1/916; A61M 1/985; A61M 2205/3306; A61M 2205/50; A61M 2205/502; A61N 2007/0034; A61N 2007/0082; A61N 7/00; A61F 13/00051
See application file for complete search history.

(56) References Cited

U.S. PATENT DOCUMENTS

| | | |
|---|---|---|
| 5,090,410 A | 2/1992 | Saper et al. |
| 5,253,654 A | 10/1993 | Thomas et al. |
| 5,635,201 A | 6/1997 | Fabo |
| 5,642,096 A | 6/1997 | Leyerer et al. |
| 5,678,448 A | 10/1997 | Fullen et al. |
| 5,690,610 A | 11/1997 | Ito et al. |
| 5,836,990 A | 11/1998 | Li |
| 6,095,992 A | 8/2000 | Augustine |
| 6,178,342 B1 | 1/2001 | Borgos et al. |
| 6,381,482 B1 | 4/2002 | Jayaraman et al. |
| 6,517,484 B1 | 2/2003 | Wilk et al. |
| 6,551,252 B2 | 4/2003 | Sackner et al. |
| 6,731,987 B1 | 5/2004 | McAdams et al. |
| 7,077,832 B2 | 7/2006 | Fleischmann |
| 7,088,591 B2 | 8/2006 | Kishimoto et al. |
| 7,201,063 B2 | 4/2007 | Taylor et al. |
| 7,206,623 B2 | 4/2007 | Blank et al. |
| 7,289,205 B2 | 10/2007 | Yaroslavsky et al. |
| 7,316,652 B2 | 1/2008 | Dalgaard et al. |
| 7,429,255 B2 | 9/2008 | Thompson |
| 7,520,875 B2 | 4/2009 | Bernabei |
| 7,521,292 B2 | 4/2009 | Rogers et al. |
| 7,569,742 B2 | 8/2009 | Haggstrom et al. |
| 7,625,117 B2 | 12/2009 | Haslett et al. |
| 7,687,678 B2 | 3/2010 | Jacobs |
| 7,838,717 B2 | 11/2010 | Haggstrom et al. |
| 7,846,141 B2 | 12/2010 | Weston |
| 7,877,866 B1 | 2/2011 | Greenberg et al. |
| 7,884,258 B2 | 2/2011 | Boehringer et al. |
| 7,904,133 B2 | 3/2011 | Gehman et al. |
| 7,922,676 B2 | 4/2011 | Daskal et al. |
| 7,942,869 B2 | 5/2011 | Houbolt et al. |
| 7,945,302 B2 | 5/2011 | McAdams |
| 8,019,401 B1 | 9/2011 | Smith et al. |
| 8,032,210 B2 | 10/2011 | Finneran et al. |
| 8,060,174 B2 | 11/2011 | Simpson et al. |
| 8,079,247 B2 | 12/2011 | Russell et al. |
| 8,111,165 B2 | 2/2012 | Ortega et al. |
| 8,116,841 B2 | 2/2012 | Bly et al. |
| 8,182,425 B2 | 5/2012 | Stamatas et al. |
| 8,207,392 B2 | 6/2012 | Haggstrom et al. |
| 8,238,996 B2 | 8/2012 | Burnes |
| 8,241,231 B2 | 8/2012 | Bausewein et al. |
| 8,332,053 B1 | 12/2012 | Patterson et al. |
| 8,333,874 B2 | 12/2012 | Currie et al. |
| 8,366,692 B2 | 2/2013 | Weston |
| 8,480,641 B2 | 7/2013 | Jacobs |
| 8,579,872 B2 | 11/2013 | Coulthard et al. |
| 8,644,911 B1 | 2/2014 | Panasyuk et al. |
| 8,663,106 B2 | 3/2014 | Stivoric et al. |
| 8,682,442 B2 | 3/2014 | McAdams |
| 8,783,948 B2 | 7/2014 | Panda et al. |
| 8,788,009 B2 | 7/2014 | Greene et al. |
| 8,800,386 B2 | 8/2014 | Taylor |
| 8,818,478 B2 | 8/2014 | Scheffler et al. |
| 8,829,263 B2 | 9/2014 | Haggstrom et al. |
| 8,848,187 B2 | 9/2014 | Uematsu et al. |
| 8,894,590 B2 | 11/2014 | Lamoise et al. |
| 8,925,392 B2 | 1/2015 | Esposito et al. |
| 8,934,957 B2 | 1/2015 | Dias et al. |
| 8,934,965 B2 | 1/2015 | Rogers et al. |
| 8,943,897 B2 | 2/2015 | Beauvais et al. |
| 8,945,030 B2 | 2/2015 | Weston |
| 8,948,839 B1 | 2/2015 | Longinotti-Buitoni et al. |
| 8,974,428 B2 | 3/2015 | Shuler et al. |
| 8,997,588 B2 | 4/2015 | Taylor |
| 9,000,251 B2 | 4/2015 | Murphy et al. |
| 9,042,075 B2 | 5/2015 | Borini et al. |
| 9,192,531 B2 | 11/2015 | Wu |
| 9,192,700 B2 | 11/2015 | Weston et al. |
| 9,204,806 B2 | 12/2015 | Stivoric et al. |
| 9,220,455 B2 | 12/2015 | Sarrafzadeh et al. |
| 9,226,402 B2 | 12/2015 | Hsu |
| 9,282,897 B2 | 3/2016 | Ross, Jr. et al. |
| 9,314,175 B2 | 4/2016 | Jacofsky et al. |
| 9,320,473 B2 | 4/2016 | Shuler |
| 9,372,123 B2 | 6/2016 | Li et al. |
| 9,378,450 B1 | 6/2016 | Mei et al. |
| 9,386,947 B2 | 7/2016 | Johnson |
| 9,393,354 B2 | 7/2016 | Freedman et al. |
| 9,402,988 B2 | 8/2016 | Buchanan et al. |
| 9,408,573 B2 | 8/2016 | Welch et al. |
| 9,427,179 B2 | 8/2016 | Mestrovic et al. |
| 9,439,599 B2 | 9/2016 | Thompson et al. |
| 9,483,726 B2 | 11/2016 | Mei et al. |
| 9,494,474 B2 | 11/2016 | Servati et al. |
| 9,511,215 B2 | 12/2016 | Skiba |
| 9,516,758 B2 | 12/2016 | Arora et al. |
| 9,526,439 B2 | 12/2016 | Connelly et al. |
| 9,554,484 B2 | 1/2017 | Rogers et al. |
| 9,572,507 B2 | 2/2017 | Moore et al. |
| 9,582,072 B2 | 2/2017 | Connor |
| 9,585,620 B2 | 3/2017 | Paquet et al. |
| 9,587,991 B2 | 3/2017 | Padiy |
| 9,592,007 B2 | 3/2017 | Nuovo et al. |
| 9,603,560 B2 | 3/2017 | Monty et al. |
| 9,610,388 B2 | 4/2017 | Aceto et al. |
| 9,613,911 B2 | 4/2017 | Rogers et al. |
| 9,629,584 B2 | 4/2017 | Macia Barber et al. |
| 9,675,238 B2 | 6/2017 | Iida et al. |
| 9,687,195 B2 | 6/2017 | Sims et al. |
| 9,717,565 B2 | 8/2017 | Blair |
| 9,829,471 B2 | 11/2017 | Hammond et al. |
| 9,907,103 B2 | 2/2018 | Chen et al. |
| 9,999,711 B2 | 6/2018 | Weston et al. |
| 10,004,643 B2 | 6/2018 | Luckemeyer et al. |
| 10,046,096 B2 | 8/2018 | Askem et al. |
| 10,080,524 B1 | 9/2018 | Xi |
| 10,086,117 B2 | 10/2018 | Locke et al. |
| 10,117,705 B2 | 11/2018 | Chernov et al. |
| 10,152,789 B2 | 12/2018 | Carnes et al. |
| 10,182,740 B2 | 1/2019 | Tonar et al. |
| 10,201,644 B2 | 2/2019 | Haggstrom et al. |
| 10,207,031 B2 | 2/2019 | Toth |
| 10,209,213 B2 | 2/2019 | Kang et al. |
| 10,285,620 B2 | 5/2019 | Jung et al. |
| 10,288,590 B2 | 5/2019 | Hammond et al. |
| 10,321,862 B2 | 6/2019 | Dalene et al. |
| 10,398,353 B2 * | 9/2019 | Addison ............ A61B 5/14542 |
| 10,568,586 B2 * | 2/2020 | Begin ................. A61B 8/5223 |
| 10,857,038 B2 | 12/2020 | Zamierowski et al. |
| 11,026,847 B2 | 6/2021 | Piotrowski et al. |
| 11,234,643 B2 * | 2/2022 | Nahmias ............... A61B 5/021 |
| 11,389,108 B2 | 7/2022 | Stroebech et al. |
| 2002/0016536 A1 | 2/2002 | Benni |
| 2002/0135752 A1 | 9/2002 | Sokolov et al. |

(56) References Cited

U.S. PATENT DOCUMENTS

| | | |
|---|---|---|
| 2003/0033032 A1 | 2/2003 | Lind et al. |
| 2003/0208148 A1 | 11/2003 | Sullivan |
| 2003/0210810 A1 | 11/2003 | Gee, Jr. et al. |
| 2003/0216630 A1 | 11/2003 | Jersey-Willuhn et al. |
| 2004/0136579 A1 | 7/2004 | Gutenev |
| 2004/0230132 A1 | 11/2004 | Shehada |
| 2005/0088832 A1 | 4/2005 | Su et al. |
| 2005/0240107 A1 | 10/2005 | Alfano et al. |
| 2005/0280531 A1 | 12/2005 | Fadem et al. |
| 2006/0052678 A1 | 3/2006 | Drinan et al. |
| 2006/0058690 A1 | 3/2006 | Bartnik et al. |
| 2006/0181791 A1 | 8/2006 | Van Beek et al. |
| 2006/0234383 A1 | 10/2006 | Gough |
| 2006/0241495 A1 | 10/2006 | Kurtz |
| 2007/0055209 A1 | 3/2007 | Patel et al. |
| 2007/0173892 A1 | 7/2007 | Fleischer et al. |
| 2007/0191754 A1 | 8/2007 | Aali |
| 2007/0260421 A1 | 11/2007 | Berner, Jr. et al. |
| 2007/0293748 A1 | 12/2007 | Engvall et al. |
| 2008/0081973 A1 | 4/2008 | Hoarau |
| 2008/0167535 A1 | 7/2008 | Stivoric et al. |
| 2008/0194928 A1* | 8/2008 | Bandic ............... A61B 5/443 600/306 |
| 2008/0258717 A1 | 10/2008 | Igney et al. |
| 2008/0287747 A1 | 11/2008 | Mestrovic et al. |
| 2008/0319282 A1 | 12/2008 | Tran |
| 2008/0319283 A1 | 12/2008 | Cotton et al. |
| 2009/0149800 A1 | 6/2009 | Durand |
| 2009/0177051 A1 | 7/2009 | Arons et al. |
| 2009/0177110 A1 | 7/2009 | Lyden et al. |
| 2009/0209830 A1 | 8/2009 | Nagle et al. |
| 2009/0234206 A1 | 9/2009 | Gaspard et al. |
| 2009/0245601 A1 | 10/2009 | Cohen et al. |
| 2010/0022990 A1 | 1/2010 | Karpowicz et al. |
| 2010/0025831 A1 | 2/2010 | Yamazaki et al. |
| 2010/0166252 A1 | 7/2010 | Ahmed et al. |
| 2010/0168727 A1 | 7/2010 | Hancock et al. |
| 2010/0268111 A1 | 10/2010 | Drinan et al. |
| 2010/0305473 A1 | 12/2010 | Yuzhakov |
| 2011/0004088 A1 | 1/2011 | Grossman |
| 2011/0015591 A1 | 1/2011 | Hanson et al. |
| 2011/0054283 A1 | 3/2011 | Shuler |
| 2011/0092958 A1 | 4/2011 | Jacobs |
| 2011/0130697 A1 | 6/2011 | Nagle et al. |
| 2011/0140703 A1 | 6/2011 | Chiao et al. |
| 2011/0190639 A1 | 8/2011 | Peltie et al. |
| 2011/0218757 A1 | 9/2011 | Callsen et al. |
| 2011/0242532 A1 | 10/2011 | McKenna |
| 2011/0245682 A1 | 10/2011 | Robinson et al. |
| 2011/0301441 A1 | 12/2011 | Bandic et al. |
| 2012/0029306 A1 | 2/2012 | Paquet et al. |
| 2012/0029307 A1 | 2/2012 | Paquet et al. |
| 2012/0029410 A1 | 2/2012 | Koenig et al. |
| 2012/0112347 A1 | 5/2012 | Eckhardt et al. |
| 2012/0165717 A1 | 6/2012 | Al Khaburi et al. |
| 2012/0190956 A1 | 7/2012 | Connolly |
| 2012/0190989 A1 | 7/2012 | Kaiser et al. |
| 2012/0265120 A1 | 10/2012 | Beisang, III et al. |
| 2012/0271265 A1 | 10/2012 | Langdon |
| 2012/0277559 A1 | 11/2012 | Kohl-Bareis et al. |
| 2012/0316538 A1 | 12/2012 | Heiser et al. |
| 2012/0330252 A1 | 12/2012 | Stokes et al. |
| 2013/0041235 A1 | 2/2013 | Rogers et al. |
| 2013/0064772 A1 | 3/2013 | Swiss et al. |
| 2013/0121544 A1 | 5/2013 | Sarrafzadeh et al. |
| 2013/0123722 A1 | 5/2013 | Pratt et al. |
| 2013/0151223 A1 | 6/2013 | Zamierowski et al. |
| 2013/0190655 A1* | 7/2013 | Jackson ............... A61B 5/442 600/587 |
| 2013/0200268 A1 | 8/2013 | Rafferty et al. |
| 2013/0261409 A1 | 10/2013 | Pathak et al. |
| 2013/0271278 A1 | 10/2013 | Duesterhoft et al. |
| 2013/0274563 A1 | 10/2013 | Duesterhoft et al. |
| 2013/0274629 A1 | 10/2013 | Duesterhoft et al. |
| 2013/0317367 A1 | 11/2013 | Shuler |
| 2014/0012108 A1 | 1/2014 | McPeak |
| 2014/0018637 A1 | 1/2014 | Bennett et al. |
| 2014/0024905 A1 | 1/2014 | Sarrafzadeh et al. |
| 2014/0031663 A1 | 1/2014 | Gallego et al. |
| 2014/0072190 A1 | 3/2014 | Wu et al. |
| 2014/0075658 A1 | 3/2014 | McGuin |
| 2014/0107495 A1 | 4/2014 | Marinelli et al. |
| 2014/0107498 A1 | 4/2014 | Bower et al. |
| 2014/0147611 A1 | 5/2014 | Ackerman, Jr. et al. |
| 2014/0203797 A1 | 7/2014 | Stivoric et al. |
| 2014/0206947 A1 | 7/2014 | Isserow et al. |
| 2014/0232516 A1 | 8/2014 | Stivoric et al. |
| 2014/0235166 A1 | 8/2014 | Molettiere et al. |
| 2014/0243709 A1 | 8/2014 | Gibson et al. |
| 2014/0296749 A1 | 10/2014 | Reid, Jr. et al. |
| 2014/0298927 A1 | 10/2014 | Allin et al. |
| 2014/0298928 A1 | 10/2014 | Duesterhoft et al. |
| 2014/0303463 A1 | 10/2014 | Robinson et al. |
| 2014/0313303 A1 | 10/2014 | Davis et al. |
| 2014/0324120 A1 | 10/2014 | Bogie et al. |
| 2014/0340857 A1 | 11/2014 | Hsu et al. |
| 2014/0343478 A1 | 11/2014 | Brennan et al. |
| 2014/0350882 A1 | 11/2014 | Everett et al. |
| 2015/0018792 A1 | 1/2015 | Marsiquet et al. |
| 2015/0025343 A1 | 1/2015 | Gareau et al. |
| 2015/0138330 A1 | 5/2015 | Krishnamoorthi |
| 2015/0141767 A1 | 5/2015 | Rogers et al. |
| 2015/0148760 A1 | 5/2015 | Dodd et al. |
| 2015/0150479 A1 | 6/2015 | Yoshino et al. |
| 2015/0182166 A1 | 7/2015 | Evans et al. |
| 2015/0223716 A1 | 8/2015 | Korkala et al. |
| 2015/0257644 A1 | 9/2015 | Cao |
| 2015/0265191 A1 | 9/2015 | Harding et al. |
| 2015/0292968 A1 | 10/2015 | Vogt et al. |
| 2015/0313476 A1 | 11/2015 | Pisani et al. |
| 2015/0313533 A1 | 11/2015 | Rapp et al. |
| 2015/0324634 A1 | 11/2015 | Brosens-Kessels et al. |
| 2015/0327777 A1 | 11/2015 | Kostic et al. |
| 2015/0335254 A1 | 11/2015 | Fastert et al. |
| 2015/0335288 A1 | 11/2015 | Toth et al. |
| 2015/0351970 A1 | 12/2015 | Dagger et al. |
| 2015/0359485 A1 | 12/2015 | Berg et al. |
| 2015/0374309 A1 | 12/2015 | Farkas et al. |
| 2016/0015962 A1 | 1/2016 | Shokoueinejad Maragheh |
| 2016/0022223 A1 | 1/2016 | Grundfest et al. |
| 2016/0029900 A1 | 2/2016 | LaPlante et al. |
| 2016/0030132 A1 | 2/2016 | Cheung et al. |
| 2016/0038045 A1 | 2/2016 | Shapiro |
| 2016/0038083 A1 | 2/2016 | Ding et al. |
| 2016/0051147 A1 | 2/2016 | Cohen et al. |
| 2016/0058380 A1 | 3/2016 | Lee et al. |
| 2016/0066854 A1 | 3/2016 | Mei et al. |
| 2016/0069743 A1 | 3/2016 | McQuilkin et al. |
| 2016/0074234 A1 | 3/2016 | Abichandi et al. |
| 2016/0081580 A1 | 3/2016 | Bergelin et al. |
| 2016/0081601 A1 | 3/2016 | Ballam et al. |
| 2016/0100790 A1 | 4/2016 | Cantu et al. |
| 2016/0100987 A1 | 4/2016 | Hartwell et al. |
| 2016/0101282 A1 | 4/2016 | Bergelin et al. |
| 2016/0129469 A1 | 5/2016 | Kulinsky et al. |
| 2016/0143534 A1 | 5/2016 | Hyde et al. |
| 2016/0157779 A1 | 6/2016 | Baxi et al. |
| 2016/0165719 A1 | 6/2016 | Li et al. |
| 2016/0166438 A1 | 6/2016 | Rovaniemi |
| 2016/0213269 A1 | 7/2016 | Lam et al. |
| 2016/0228049 A1 | 8/2016 | Nackaerts et al. |
| 2016/0232807 A1 | 8/2016 | Ghaffari et al. |
| 2016/0242331 A1 | 8/2016 | Park et al. |
| 2016/0249810 A1 | 9/2016 | Darty et al. |
| 2016/0262672 A1 | 9/2016 | Hammond et al. |
| 2016/0262687 A1 | 9/2016 | Vaidyanathan et al. |
| 2016/0270700 A1 | 9/2016 | Baxi et al. |
| 2016/0287177 A1 | 10/2016 | Huppert et al. |
| 2016/0302729 A1 | 10/2016 | Starr et al. |
| 2016/0310023 A1 | 10/2016 | Chachisvilis et al. |
| 2016/0317057 A1 | 11/2016 | Li et al. |
| 2016/0331263 A1 | 11/2016 | Cailler et al. |
| 2016/0331322 A1 | 11/2016 | Son et al. |
| 2016/0338591 A1 | 11/2016 | Lachenbruch et al. |

(56) References Cited

U.S. PATENT DOCUMENTS

| | | |
|---|---|---|
| 2016/0354001 A1 | 12/2016 | Buckley et al. |
| 2016/0367189 A1 | 12/2016 | Aimone et al. |
| 2016/0367192 A1 | 12/2016 | Iyengar et al. |
| 2016/0367406 A1 | 12/2016 | Barnett |
| 2017/0000407 A1 | 1/2017 | Saxby et al. |
| 2017/0007853 A1 | 1/2017 | Alford et al. |
| 2017/0014556 A1 | 1/2017 | Haggstrom et al. |
| 2017/0027498 A1 | 2/2017 | Larson et al. |
| 2017/0079530 A1 | 3/2017 | Dimaio et al. |
| 2017/0079740 A1 | 3/2017 | Hufnagel et al. |
| 2017/0086519 A1 | 3/2017 | Vigano et al. |
| 2017/0086709 A1 | 3/2017 | Khine et al. |
| 2017/0095208 A1 | 4/2017 | Oberleitner et al. |
| 2017/0119258 A1 | 5/2017 | Kotanko et al. |
| 2017/0146474 A1 | 5/2017 | Bedell et al. |
| 2017/0156594 A1 | 6/2017 | Stivoric et al. |
| 2017/0156621 A1 | 6/2017 | Bettinger et al. |
| 2017/0156658 A1 | 6/2017 | Maharbiz et al. |
| 2017/0161893 A1* | 6/2017 | Carnes .................. G06T 11/008 |
| 2017/0164865 A1 | 6/2017 | Rafferty et al. |
| 2017/0164876 A1 | 6/2017 | Hyde et al. |
| 2017/0172439 A1 | 6/2017 | Zhu et al. |
| 2017/0202711 A1 | 7/2017 | Cernasov et al. |
| 2017/0224271 A1 | 8/2017 | Lachenbruch et al. |
| 2017/0231015 A1 | 8/2017 | Jang et al. |
| 2017/0238842 A1* | 8/2017 | Jacquel ................ A61B 5/7221 |
| 2017/0258972 A1 | 9/2017 | Weston |
| 2017/0304510 A1 | 10/2017 | Askem et al. |
| 2017/0319075 A1 | 11/2017 | Homan et al. |
| 2017/0326004 A1 | 11/2017 | Long et al. |
| 2017/0367644 A1 | 12/2017 | Sharman et al. |
| 2018/0008177 A1 | 1/2018 | Shimuta et al. |
| 2018/0055359 A1 | 3/2018 | Shamim et al. |
| 2018/0055697 A1 | 3/2018 | Mihali et al. |
| 2018/0056087 A1 | 3/2018 | Ribiero et al. |
| 2018/0070880 A1 | 3/2018 | Trembly et al. |
| 2018/0074547 A1 | 3/2018 | Smadi et al. |
| 2018/0116877 A1 | 5/2018 | Ineichen |
| 2018/0132287 A1 | 5/2018 | Cheng et al. |
| 2018/0192514 A1 | 7/2018 | Seo |
| 2018/0200414 A1 | 7/2018 | Askem et al. |
| 2018/0206758 A1 | 7/2018 | Feldkamp et al. |
| 2018/0235484 A1 | 8/2018 | Mozdzierz |
| 2018/0296397 A1 | 10/2018 | Askem et al. |
| 2018/0317774 A1* | 11/2018 | Sgroi, Jr. ............ A61B 10/0045 |
| 2019/0001032 A1 | 1/2019 | Weston et al. |
| 2019/0021911 A1 | 1/2019 | Askem et al. |
| 2019/0060126 A1 | 2/2019 | Ribble et al. |
| 2019/0076298 A1 | 3/2019 | Quintanar et al. |
| 2019/0083025 A1 | 3/2019 | Aung et al. |
| 2019/0117379 A1* | 4/2019 | Quirós .................. A61B 5/107 |
| 2019/0133812 A1 | 5/2019 | Seres et al. |
| 2019/0134280 A1 | 5/2019 | Toth |
| 2019/0159938 A1 | 5/2019 | Askem et al. |
| 2019/0175098 A1 | 6/2019 | Burns |
| 2019/0192066 A1 | 6/2019 | Schoess et al. |
| 2019/0231939 A1 | 8/2019 | Askem et al. |
| 2019/0290496 A1 | 9/2019 | Brownhill et al. |
| 2019/0388142 A1 | 12/2019 | Chernov et al. |
| 2020/0000394 A1 | 1/2020 | Hutchinson et al. |
| 2020/0147407 A1 | 5/2020 | Efremkin |
| 2020/0330258 A1 | 10/2020 | Hansen et al. |
| 2021/0212855 A1 | 7/2021 | Hansen et al. |
| 2022/0079814 A1 | 3/2022 | Chen et al. |

FOREIGN PATENT DOCUMENTS

| | | | |
|---|---|---|---|
| CN | 106102322 | 11/2016 | |
| DE | 10 2012 211015 | 1/2014 | |
| DE | 10 2013 013013 | 2/2015 | |
| EP | 2 454 990 | 5/2012 | |
| EP | 2 565 630 | 3/2013 | |
| EP | 2 574 275 | 4/2013 | |
| EP | 1 854 342 | 6/2014 | |
| EP | 1 734 858 | 7/2014 | |
| EP | 2 451 349 | 4/2016 | |
| EP | 2 941 195 | 12/2016 | |
| EP | 3 231 478 | 10/2017 | |
| EP | 3 409 190 | 12/2018 | |
| EP | 3 499 510 | 6/2019 | |
| GB | 1476894 | 6/1977 | |
| GB | 2316171 | 2/1998 | |
| GB | 2563602 | 12/2018 | |
| JP | 2009-225863 | 10/2009 | |
| KR | 10 2012 0119523 | 10/2012 | |
| KR | 101224629 B1 | 1/2013 | |
| KR | 10 2014 0024743 | 3/2014 | |
| KR | 10 2014 0058041 | 5/2014 | |
| KR | 10 2016 0071044 | 6/2016 | |
| KR | 20190105898 A | 9/2019 | |
| NL | 1 027 236 | 4/2006 | |
| WO | WO 2000/021433 | 4/2000 | |
| WO | WO 2000/043046 | 7/2000 | |
| WO | WO-0043046 A2 | 7/2000 | |
| WO | WO 2003/067229 | 8/2003 | |
| WO | WO-03105689 A1 * | 12/2003 | ........... A61B 5/0048 |
| WO | WO 2006/041997 | 4/2006 | |
| WO | WO 2007/030379 | 3/2007 | |
| WO | WO-2007144810 A1 | 12/2007 | |
| WO | WO 2008/006150 | 1/2008 | |
| WO | WO 2008/010604 | 1/2008 | |
| WO | WO 2009/052607 | 4/2009 | |
| WO | WO 2009/120951 | 10/2009 | |
| WO | WO 2009/141777 | 11/2009 | |
| WO | WO 2010/020919 | 2/2010 | |
| WO | WO 2010/105053 | 9/2010 | |
| WO | WO 2011/082420 | 7/2011 | |
| WO | WO 2011/113070 | 9/2011 | |
| WO | WO 2011/123848 | 10/2011 | |
| WO | WO 2012/141999 | 10/2012 | |
| WO | WO 2013/026999 | 2/2013 | |
| WO | WO 2013/044226 | 3/2013 | |
| WO | WO 2013/155193 | 10/2013 | |
| WO | WO 2014/036577 | 3/2014 | |
| WO | WO-2014116816 A1 | 7/2014 | |
| WO | WO 2015/112095 | 7/2015 | |
| WO | WO 2015/168720 | 11/2015 | |
| WO | WO 2016/014384 | 1/2016 | |
| WO | WO 2016/025438 | 2/2016 | |
| WO | WO 2016/030752 | 3/2016 | |
| WO | WO 2016/058032 | 4/2016 | |
| WO | WO-2016073777 A1 | 5/2016 | |
| WO | WO 2016/100218 | 6/2016 | |
| WO | WO 2016/109744 | 7/2016 | |
| WO | WO 2016/110564 | 7/2016 | |
| WO | WO-2016164904 A1 | 10/2016 | |
| WO | WO 2016/187136 | 11/2016 | |
| WO | WO 2016/205872 | 12/2016 | |
| WO | WO 2016/205881 | 12/2016 | |
| WO | WO 2017/021006 | 2/2017 | |
| WO | WO 2017/021965 | 2/2017 | |
| WO | WO 2017/033058 | 3/2017 | |
| WO | WO 2017/037479 | 3/2017 | |
| WO | WO 2017/041014 | 3/2017 | |
| WO | WO 2017/041386 | 3/2017 | |
| WO | WO 2017/041387 | 3/2017 | |
| WO | WO-2017041385 A1 | 3/2017 | |
| WO | WO 2017/119996 | 7/2017 | |
| WO | WO 2017/205728 | 11/2017 | |
| WO | WO 2017/214188 | 12/2017 | |
| WO | WO 2018/035612 | 3/2018 | |
| WO | WO 2018/064569 | 4/2018 | |
| WO | WO-2018060417 A1 | 4/2018 | |
| WO | WO 2018/115461 | 6/2018 | |
| WO | WO 2018/144938 | 8/2018 | |
| WO | WO 2018/144941 | 8/2018 | |
| WO | WO 2018/144943 | 8/2018 | |
| WO | WO 2018/144946 | 8/2018 | |
| WO | WO 2018/162728 | 9/2018 | |
| WO | WO 2018/162732 | 9/2018 | |
| WO | WO 2018/162735 | 9/2018 | |
| WO | WO 2018/162736 | 9/2018 | |
| WO | WO 2018/185138 | 10/2018 | |
| WO | WO 2018/189265 | 10/2018 | |

(56) References Cited

FOREIGN PATENT DOCUMENTS

| | | |
|---|---|---|
| WO | WO 2018/209090 | 11/2018 |
| WO | WO 2018/210692 | 11/2018 |
| WO | WO 2018/210693 | 11/2018 |
| WO | WO 2018/211458 | 11/2018 |
| WO | WO 2018/234443 | 12/2018 |
| WO | WO 2019/020550 | 1/2019 |
| WO | WO 2019/020551 | 1/2019 |
| WO | WO 2019/020666 | 1/2019 |
| WO | WO 2019/030384 | 2/2019 |
| WO | WO 2019/048624 | 3/2019 |
| WO | WO 2019/048626 | 3/2019 |
| WO | WO 2019/048638 | 3/2019 |
| WO | WO 2019/063481 | 4/2019 |
| WO | WO 2019/063488 | 4/2019 |
| WO | WO 2019/067264 | 4/2019 |
| WO | WO 2019/072531 | 4/2019 |
| WO | WO 2019/076967 | 4/2019 |
| WO | WO 2019/096828 | 5/2019 |
| WO | WO 2019/140441 | 7/2019 |
| WO | WO 2019/140444 | 7/2019 |
| WO | WO 2019/140448 | 7/2019 |
| WO | WO 2019/140449 | 7/2019 |
| WO | WO-2019193141 A1 | 10/2019 |
| WO | WO-2019216883 A1 | 11/2019 |

OTHER PUBLICATIONS

Invitation to Pay Additional Fees and Partial Search Report, re PCT Application No. PCT/EP2018/062206, dated Aug. 29, 2018.
International Preliminary Report on Patentability for Application No. PCT/EP2018/062206, dated Nov. 28, 2019, 21 pages.
Mehmood N., et al., "Applications Of Modern Sensors And Wireless Technology In Effective Wound Management: Modern Sensors And Wireless Technology," Journal of Biomedical Materials Research Part B, vol. 102, May 1, 2014, XP055739544, pp. 885-895.
Aubakir, B. et al., "Vital Sign Monitoring Utilizing Eulerian Video Magnification and Thermography", 2016 38th Annual International Conference of the IEEE Engineering in Medicine and Biology Society, Aug. 16, 2016, pp. 3527-3530, in 4 pages.
International Search Report and Written Opinion, re PCT Application No. PCT/EP2018/062206, dated Oct. 23, 2018.
Mcleod, A. et al., "Motion Magnification for Endoscopic Surgery", Progress in Biomedical Optics and Imaging, SPIE—International Society for Optical Engineering, Mar. 12, 2014, vol. 9036, in 8 pages.
"Little Miss Plasters", kidstravelclub.co.uk., accessed Aug. 26, 2016, in 2 pages. URL: http://www.kidstravelclub.co.uk/little-miss-girls-childrens-plasters.
Bandodkar, A. et al., "Battery-free, skin-interfaced microfluidic/electronic systems for simultaneous electrochemical, colorimetric, and volumetric analysis of sweat", Science Advances, vol. 5(1), Jan. 18, 2019, in 16 pages. URL: http://advances.sciencemag.org/content/5/1/eaav3294.
Cauwe, M. et al., "Technology development for a low-cost, roll-to-roll chip embedding solution based on PET foils", 18th European Microelectronics and Packaging Conference (EMPC), IEEE, Sep. 12, 2011, in 6 pages.
Farooqui, M. et al., "Low Cost Inkjet Printed Smart Bandage for Wireless Monitoring of Chronic Wounds", Scientific Reports, vol. 6, Jun. 29, 2016, in 14 pages.
Geng, Y. et al., "A Hybrid Low Power Biopatch for Body Surface Potential Measurement", IEEE Journal of Biomedical and Health Informatics, vol. 17(3), May 1, 2013, XP011506375.
Iannetta, R.A. et al., "Successful case histories of polymer based circuitry on flexible film substrates", Electro/94 International Conference Proceedings Combined Volumes, IEEE, May 10-12, 1994, XP010149465.
Jinto, G. et al., "Reliability of Plastic-Encapsulated Electronic Components in Supersaturated Steam Environments", IEEE Transactions on Components, Packaging, and Manufacturing Technology, vol. 5, No. 10, Oct. 2015, in 9 pages.
Lu, B. et al., "A study of the autofluorescence of parylene materials for [mu]TAS applications", Lab on Chip, vol. 10, No. 14, Jul. 2010, pp. 1826-1834, in 9 pages.
Mostafalu, P. et al., "Wireless Flexible Smart Bandage for Continuous Monitoring of Wound Oxygenation", IEEE Transactions on Biomedical Circuits and Systems, vol. 9, No. 5, Oct. 2015, pp. 670-677, in 8 pages.
Narusawa, H., "The corona discharge causes short destruction that had bad influence on a power switching circuit", Adphox Corporation, Jan. 1, 2009, in 12 pages. URL: http://www.adphox.co.jp/keisokuki/ke-english-corona/CORONA_DISCHARGE_EN.pdf.
Raviglione, A. et al., "Real-Time Smart Textile-Based System to Monitor Pressure Offloading of Diabetic Foot Ulcers", Journal of Diabetes Science and Technology, vol. 11, Sep. 2017, in 5 pages.
Rose, D. et al., "Adhesive RFID Sensor Patch for Monitoring of Sweat Electrolytes", IEEE Transactions on Biomedical Engineering, vol. 62(6), Jun. 2015 (first published Nov. 11, 2015), in 9 pages.
Wakita, J. et al., "Variations in Optical Absorption and Fluorescence Spectra for Polyimide Thin Films Caused by Structural Isomerism", J. Photopolym. Sci. Technol. Jan. 1, 2003, in 1 page.
Willis, B., "Conformal Coating Inspection & Coating Faults", Vision Engineering, Jul. 21, 2016, in 35 pages. URL: http://www.visioneng.com/wp-content/uploads/2017/11/Confirmal-Coating-Inspection-and-Defects.21JUL16.pdf.
Willis, B., "Guide to Conformal Coating & Cleaning Defects Contents", Mar. 1, 2014, in 31 pages. URL: http://coatingguide.smartgroup.org/Files%20pdf/Coating%20Defects%20V2%2014March2014.pdf.

\* cited by examiner

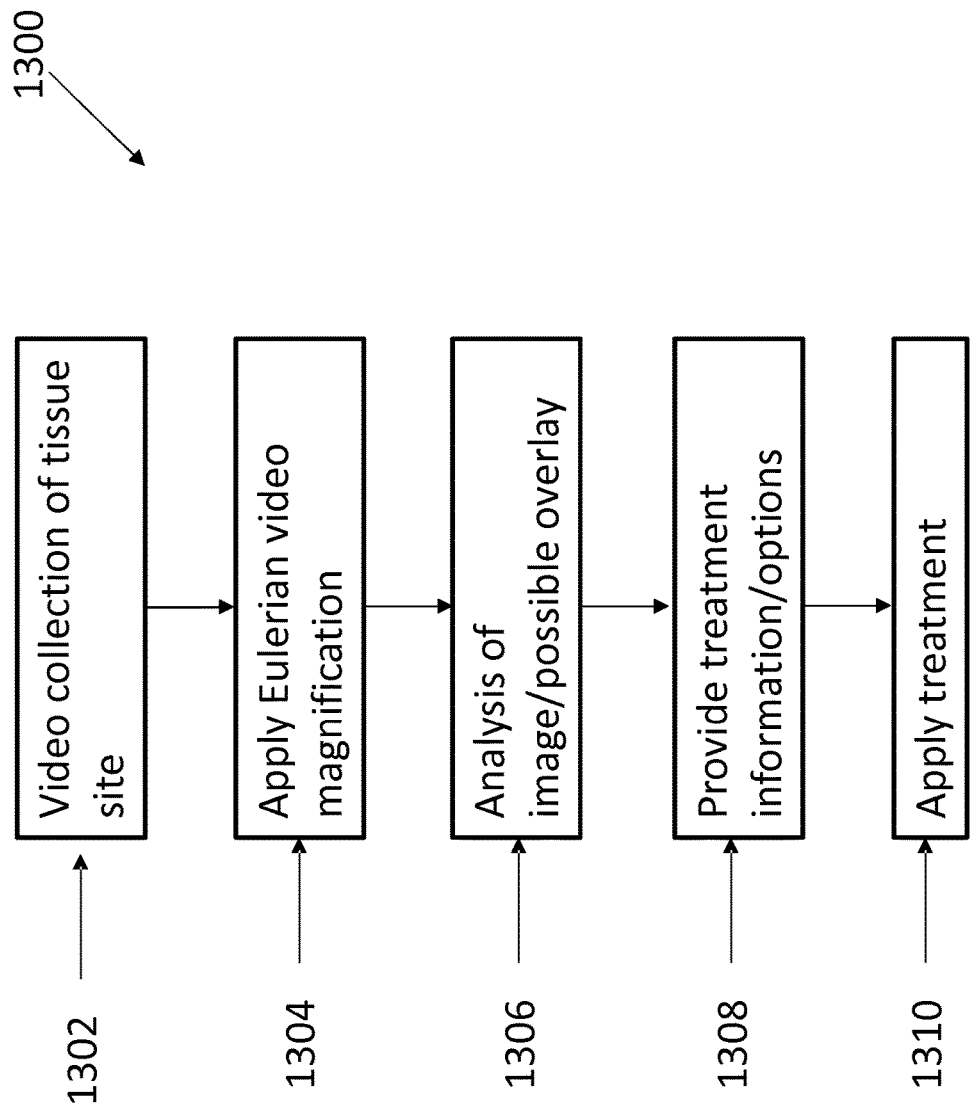

WOUND ANALYSIS DEVICE AND METHOD

CROSS-REFERENCE TO RELATED APPLICATIONS

This application is a U.S. national stage application of International Patent Application No. PCT/EP2018/062206, filed May 11, 2018, which claims the benefit of U.S. Provisional Application No. 62/506,551, filed May 15, 2017; the disclosure of which is hereby incorporated by reference in its entirety.

BACKGROUND

Technical Field

Embodiments described herein relate to apparatuses, systems, and methods for the treatment of wounds, for example monitoring wounds and providing an appropriate treatment.

Description of the Related Art

Modern wound treatment may involve multiple approaches including the use of various dressings, irrigants, debridement techniques, chemicals that promote healing, medicaments, and treatment negative pressure wound therapy (NPWT). NPWT systems currently known in the art commonly involve placing a cover that is impermeable or semi-permeable to fluids over the wound, using various means to seal the cover to the tissue of the patient surrounding the wound, and connecting a source of negative pressure (such as a vacuum pump) to the cover in a manner so that negative pressure is created and maintained under the cover. Typically, wounds are monitoring by the naked eye and treatment is modified based on the experience of the clinical practitioner.

However, prior art wound therapy provide little automated visualization or information on the condition of a wound site or a tissue site, particularly early in the process before a wound has actually formed, for example during the early stages of pressure ulcer formation. Further, existing techniques for the evaluation of intact tissue and wounds are restricted by the limitations of the human eye or more rarely, standard videography techniques. Therefore, existing techniques may provide inadequate information about the state of tissue before a wound exists; thus, improved methods and techniques for evaluating/detecting changes within wounds and tissue are needed.

Further, while nearly all areas of medicine may benefit from improved information regarding the state of the tissue, organ, or system to be treated, particularly if such information is gathered in real-time during treatment, many types of treatments are still routinely performed without the use of sensor data collection. Instead, such treatments rely upon visual inspection by a caregiver or other limited means rather than quantitative sensor data. For example, in the case of wound treatment via dressings and/or negative pressure wound therapy, data collection is generally limited to visual inspection by a caregiver and often the underlying wounded tissue may be obscured by bandages or other visual impediments. Even intact, unwounded skin may have underlying damage that is not visible to the naked eye, such as a compromised vascular or deeper tissue damage that may lead to an ulcer. Similar to wound treatment, during orthopedic treatments requiring the immobilization of a limb with a cast or other encasement, only limited information is gathered on the underlying tissue. In instances of internal tissue repair, such as a bone plate, continued direct sensor-driven data collection is not performed. Further, braces and/or sleeves used to support musculoskeletal function do not monitor the functions of the underlying muscles or the movement of the limbs. Outside of direct treatments, common hospital room items such as beds and blankets could be improved by adding capability to monitor patient parameters.

Therefore, there is a need for improved sensor monitoring, particularly through the use of sensor-enabled substrates which can be incorporated into existing treatment regimes.

SUMMARY

Certain disclosed embodiments relate to devices, methods, and systems for monitoring tissues. It will be understood by one of skill of art that application of the devices, methods, and systems described herein are not limited to a particular tissue or a particular injury.

In certain embodiments, a treatment system may comprise a visualization sensor configured to be positioned over a tissue site, the visualization sensor configured to collect video data of the tissue site, an output configured to provide an alert, and a controller in communication with both the visualization sensor and the output, the controller configured to: amplify the video data by Eulerian video magnification, determine a treatment parameter from the amplified video data and cause the output to provide an alert in response to determining that the treatment parameter differs from a threshold.

In some embodiments, the threshold corresponds to a probability of occurrence of a pressure injury. The controller may be contained within a smartphone. The visualization sensor may be configured to communicate wirelessly with the controller. The controller may be configured to communicate wirelessly with the output. The controller can be configured to compare the treatment parameter to a plurality of thresholds. The visualization sensor may comprise an RGB detector. The alert may comprise an audible alarm and/or a visual alarm.

The controller may be configured to determine the tissue parameter by calculating the change in a red value between two or more frames of video data.

In certain embodiments, a system for identifying incision sites may comprise: a visualization sensor configured to be positioned over a tissue site, the visualization sensor configured to collect video data of the tissue site, a controller in communication with the visualization sensor, the controller configured to: amplify the video data by Eulerian video magnification, identify Langer Lines in the tissue site from the amplified video data, map the Langer Lines over the video data of the tissue site; and display the Langer Lines on a display.

The system may further comprise an output configured to provide an incision site alert. The incision site alert may comprise an orientation and a position.

In certain embodiments, a system for monitoring the treatment of a tissue site, may comprise: an ultrasound generator, the ultrasound generator configured to deliver therapeutic ultrasound to an internal tissue site, and a visualization sensor configured to be positioned over the internal tissue site, the visualization sensor configured to collect magnetic induction tomography video data of the tissue site. The system may comprise an output configured to provide an alert when the magnetic induction tomography video data exceeds a threshold.

In some embodiments, a method of operating a treatment system comprising a visualization sensor and a controller may comprise: by the visualization sensor positioned over a tissue site, collecting video data of the tissue site, and by the controller: amplifying the video data by Eulerian video magnification, determining a treatment parameter from the amplified video data, and causing provision of an alert in response to determining that the treatment parameter differs from a threshold.

In some embodiments, a method of operating a treatment system comprising a visualization sensor and a controller may comprise: by the visualization sensor positioned over a tissue site, collecting video data of the tissue site, and by the controller: amplifying the video data by Eulerian video magnification, determining a red-delta value from the amplified video data; and causing a provision of an alert if the red-delta value indicates the presence of a blood vessel in the tissue site.

Other embodiments are described below.

BRIEF DESCRIPTION OF THE DRAWINGS

FIG. 6 illustrates an embodiment of a wound diagnostic system.

DETAILED DESCRIPTION

Figure 1:
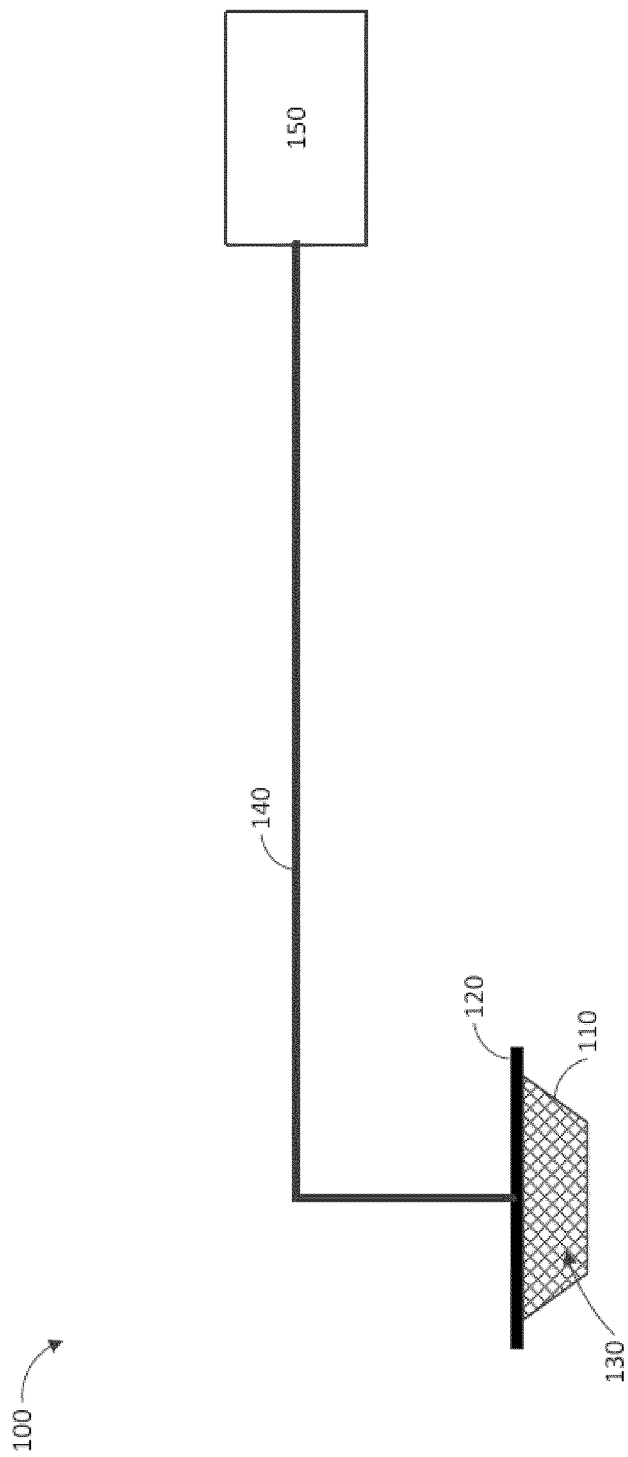
FIG. 1 illustrates a reduced pressure wound therapy system according to some embodiments.

Embodiments disclosed herein relate to apparatuses and methods of monitoring and treating biological tissue with sensor-enabled substrates. The embodiments disclosed herein are not limited to treatment or monitoring of a particular type of tissue or injury, instead the sensor-enabled technologies disclosed herein are broadly applicable to any type of therapy that may benefit from sensor-enabled substrates. Some implementations utilize sensors and data collection relied upon by health care providers to make both diagnostic and patient management decisions.

Some embodiments disclosed herein relate to the use of sensors mounted on or embedded within substrates configured to be used in the treatment of both intact and damaged human or animal tissue. Such sensors may collect information about the surrounding tissue and transmit such information to a computing device or a caregiver to be utilized in further treatment. In certain embodiments, such sensors may be attached to the skin anywhere on the body, including areas for monitoring arthritis, temperature, or other areas that may be prone to problems and require monitoring. Sensors disclosed herein may also incorporate markers, such as radiopaque markers, to indicate the presence of the device, for example prior to performing an MRI or other technique.

The sensor embodiments disclosed herein may be used in combination with clothing. Non-limiting examples of clothing for use with embodiments of the sensors disclosed herein include shirts, pants, trousers, dresses, undergarments, outer-garments, gloves, shoes, hats, and other suitable garments. In certain embodiments, the sensor embodiments disclosed herein may be welded into or laminated into/onto the particular garments. The sensor embodiments may be printed directly onto the garment and/or embedded into the fabric. Breathable and printable materials such as microporous membranes may also be suitable.

Sensor embodiments disclosed herein may be incorporated into cushioning or bed padding, such as within a hospital bed, to monitor patient characteristics, such as any characteristic disclosed herein. In certain embodiments, a disposable film containing such sensors could be placed over the hospital bedding and removed/replaced as needed.

In some implementations, the sensor embodiments disclosed herein may incorporate energy harvesting, such that the sensor embodiments are self-sustaining. For example, energy may be harvested from thermal energy sources, kinetic energy sources, chemical gradients, or any suitable energy source.

The sensor embodiments disclosed herein may be utilized in rehabilitation devices and treatments, including sports medicine. For example, the sensor embodiments disclosed herein may be used in braces, sleeves, wraps, supports, and other suitable items. Similarly, the sensor embodiments disclosed herein may be incorporated into sporting equipment, such as helmets, sleeves, and/or pads. For example, such sensor embodiments may be incorporated into a protective helmet to monitor characteristics such as acceleration, which may be useful in concussion diagnosis.

The sensor embodiments disclosed herein may be used in coordination with surgical devices, for example, the NAVIO surgical system by Smith & Nephew Inc. In implementations, the sensor embodiments disclosed herein may be in communication with such surgical devices to guide placement of the surgical devices. In some implementations, the sensor embodiments disclosed herein may monitor blood flow to or away from the potential surgical site or ensure that there is no blood flow to a surgical site. Further surgical data may be collected to aid in the prevention of scarring and monitor areas away from the impacted area.

To further aid in surgical techniques, the sensors disclosed herein may be incorporated into a surgical drape to provide information regarding tissue under the drape that may not be immediately visible to the naked eye. For example, a sensor embedded flexible drape may have sensors positioned advantageously to provide improved area-focused data collection. In certain implementations, the sensor embodiments disclosed herein may be incorporated into the border or interior of a drape to create fencing to limit/control the surgical theater.

Sensor embodiments as disclosed herein may also be utilized for pre-surgical assessment. For example, such sensor embodiments may be used to collect information about a potential surgical site, such as by monitoring skin and the underlying tissues for a possible incision site. For example, perfusion levels or other suitable characteristics may be monitored at the surface of the skin and deeper in the tissue to assess whether an individual patient may be at risk for surgical complications. Sensor embodiments such as those disclosed herein may be used to evaluate the presence of microbial infection and provide an indication for the use of antimicrobials. Further, sensor embodiments disclosed herein may collect further information in deeper tissue, such as identifying pressure ulcer damage and/or the fatty tissue levels.

The sensor embodiments disclosed herein may be utilized in cardiovascular monitoring. For example, such sensor embodiments may be incorporated into a flexible cardiovascular monitor that may be placed against the skin to monitor characteristics of the cardiovascular system and communicate such information to another device and/or a caregiver. For example, such a device may monitor pulse rate, oxygenation of the blood, and/or electrical activity of the heart. Similarly, the sensor embodiments disclosed herein may be utilized for neurophysiological applications, such as monitoring electrical activity of neurons.

The sensor embodiments disclosed herein may be incorporated into implantable devices, such as implantable orthopedic implants, including flexible implants. Such sensor embodiments may be configured to collect information regarding the implant site and transmit this information to an external source. In some embodiments, an internal source may also provide power for such an implant.

The sensor embodiments disclosed herein may also be utilized for monitoring biochemical activity on the surface of the skin or below the surface of the skin, such as lactose buildup in muscle or sweat production on the surface of the skin. In some embodiments, other characteristics may be monitored, such as glucose concentration, urine concentration, tissue pressure, skin temperature, skin surface conductivity, skin surface resistivity, skin hydration, skin maceration, and/or skin ripping.

Sensor embodiments as disclosed herein may be incorporated into Ear, Nose, and Throat (ENT) applications. For example, such sensor embodiments may be utilized to monitor recovery from ENT-related surgery, such as wound monitoring within the sinus passage.

As described in greater detail below, the sensor embodiments disclosed herein may encompass sensor printing technology with encapsulation, such as encapsulation with a polymer film Such a film may be constructed using any polymer described herein, such as polyurethane. Encapsulation of the sensor embodiments may provide waterproofing of the electronics and protection from local tissue, local fluids, and other sources of potential damage.

In certain embodiments, the sensors disclosed herein may be incorporated into an organ protection layer such as disclosed below. Such a sensor-embedded organ protection layer may both protect the organ of interest and confirm that the organ protection layer is in position and providing protection. Further, a sensor-embedded organ protection layer may be utilized to monitor the underlying organ, such as by monitoring blood flow, oxygenation, and other suitable markers of organ health. In some embodiments, a sensor-enabled organ protection layer may be used to monitor a transplanted organ, such as by monitoring the fat and muscle content of the organ. Further, sensor-enabled organ protection layers may be used to monitor an organ during and after transplant, such as during rehabilitation of the organ.

The sensor embodiments disclosed herein may be incorporated into treatments for wounds (disclosed in greater detail below) or in a variety of other applications. Non-limiting examples of additional applications for the sensor embodiments disclosed herein include: monitoring and treatment of intact skin, cardiovascular applications such as monitoring blood flow, orthopedic applications such as monitoring limb movement and bone repair, neurophysiological applications such as monitoring electrical impulses, and any other tissue, organ, system, or condition that may benefit from improved sensor-enabled monitoring.

Wound Therapy

Some embodiments disclosed herein relate to wound therapy for a human or animal body. Therefore, any reference to a wound herein can refer to a wound on a human or animal body, and any reference to a body herein can refer to a human or animal body. The disclosed technology embodiments may relate to preventing or minimizing damage to physiological tissue or living tissue, or to the treatment of damaged tissue (for example, a wound as described herein) wound with or without reduced pressure, including for example a source of negative pressure and wound dressing components and apparatuses. The apparatuses and components comprising the wound overlay and packing materials or internal layers, if any, are sometimes collectively referred to herein as dressings. In some embodiments, the wound dressing can be provided to be utilized without reduced pressure.

Some embodiments disclosed herein relate to wound therapy for a human or animal body. Therefore, any reference to a wound herein can refer to a wound on a human or animal body, and any reference to a body herein can refer to a human or animal body. The disclosed technology embodiments may relate to preventing or minimizing damage to physiological tissue or living tissue, or to the treatment of damaged tissue (for example, a wound as described herein).

As used herein the expression "wound" may include an injury to living tissue may be caused by a cut, blow, or other impact, typically one in which the skin is cut or broken. A wound may be a chronic or acute injury. Acute wounds occur as a result of surgery or trauma. They move through the stages of healing within a predicted timeframe. Chronic wounds typically begin as acute wounds. The acute wound can become a chronic wound when it does not follow the healing stages resulting in a lengthened recovery. It is believed that the transition from acute to chronic wound can be due to a patient being immuno-compromised.

Chronic wounds may include for example: venous ulcers (such as those that occur in the legs), which account for the majority of chronic wounds and mostly affect the elderly, diabetic ulcers (for example, foot or ankle ulcers), peripheral arterial disease, pressure ulcers, or epidermolysis bullosa (EB).

Examples of other wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like.

Wounds may also include a deep tissue injury. Deep tissue injury is a term proposed by the National Pressure Ulcer Advisory Panel (NPUAP) to describe a unique form of pressure ulcers. These ulcers have been described by clinicians for many years with terms such as purple pressure ulcers, ulcers that are likely to deteriorate and bruises on bony prominences.

Wound may also include tissue at risk of becoming a wound as discussed herein. For example, tissue at risk may include tissue over a bony protuberance (at risk of deep tissue injury/insult) or pre-surgical tissue (for example, knee tissue) that may has the potential to be cut (for example, for joint replacement/surgical alteration/reconstruction).

Some embodiments relate to methods of treating a wound with the technology disclosed herein in conjunction with one or more of the following: advanced footwear, turning a patient, offloading (such as, offloading diabetic foot ulcers), treatment of infection, systemix, antimicrobial, antibiotics, surgery, removal of tissue, affecting blood flow, physiotherapy, exercise, bathing, nutrition, hydration, nerve stimulation, ultrasound, electrostimulation, oxygen therapy, microwave therapy, active agents ozone, antibiotics, antimicrobials, or the like.

Alternatively or additionally, a wound may be treated using topical negative pressure and/or traditional advanced wound care, which is not aided by the using of applied negative pressure (may also be referred to as non-negative pressure therapy).

Advanced wound care may include use of an absorbent dressing, an occlusive dressing, use of an antimicrobial and/or debriding agents in a wound dressing or adjunct, a pad (for example, a cushioning or compressive therapy, such as stockings or bandages), or the like.

In some embodiments, treatment of such wounds can be performed using traditional wound care, wherein a dressing can be applied to the wound to facilitate and promote healing of the wound.

Some embodiments relate to methods of manufacturing a wound dressing comprising providing a wound dressing as disclosed herein.

The wound dressings that may be utilized in conjunction with the disclosed technology include any known dressing in the art. The technology is applicable to negative pressure therapy treatment as well as non-negative pressure therapy treatment.

In some embodiments, a wound dressing comprises one or more absorbent layer(s). The absorbent layer may be a foam or a superabsorbent.

In some embodiments, wound dressings may comprise a dressing layer including a polysaccharide or modified polysaccharide, a polyvinylpyrrolidone, a polyvinyl alcohol, a polyvinyl ether, a polyurethane, a polyacrylate, a polyacrylamide, collagen, or gelatin or mixtures thereof. Dressing layers comprising the polymers listed are known in the art as being useful for forming a wound dressing layer for either negative pressure therapy or non-negative pressure therapy.

In some embodiments, the polymer matrix may be a polysaccharide or modified polysaccharide.

In some embodiments, the polymer matrix may be a cellulose. Cellulose material may include hydrophilically modified cellulose such as methyl cellulose, carboxymethyl cellulose (CMC), carboxymethyl cellulose (CEC), ethyl cellulose, propyl cellulose, hydroxyethyl cellulose, hydroxypropyl cellulose, hydroxypropylmethyl cellulose, carboxyethyl sulphonate cellulose, cellulose alkyl sulphonate, or mixtures thereof.

In certain embodiments, cellulose material may be cellulose alkyl sulphonate. The alkyl moiety of the alkyl sulphonate substituent group may have an alkyl group having 1 to 6 carbon atoms, such as methyl, ethyl, propyl, or butyl. The alkyl moiety may be branched or unbranched, and hence suitable propyl sulphonate substituents may be 1- or 2-methyl-ethylsulphonate. Butyl sulphonate substituents may be 2-ethyl-ethylsulphonate, 2,2-dimethyl-ethylsulphonate, or 1,2-dimethyl-ethylsulphonate. The alkyl sulphonate substituent group may be ethyl sulphonate. The cellulose alkyl sulphonate is described in WO10061225, US2016/114074, US2006/0142560, or U.S. Pat. No. 5,703,225, the disclosures of which are hereby incorporated by reference in their entirety.

Cellulose alkyl sulfonates may have varying degrees of substitution, the chain length of the cellulose backbone structure, and the structure of the alkyl sulfonate substituent. Solubility and absorbency are largely dependent on the degree of substitution: as the degree of substitution is increased, the cellulose alkyl sulfonate becomes increasingly soluble. It follows that, as solubility increases, absorbency increases.

In some embodiments, a wound dressing also comprises a top or cover layer.

The thickness of the wound dressing disclosed herein may be between 1 to 20, or 2 to 10, or 3 to 7 mm.

In some embodiments, the disclosed technology may be used in conjunction with a non-negative pressure dressing. A non-negative pressure wound dressing suitable for providing protection at a wound site may comprise:
  an absorbent layer for absorbing wound exudate and
  an obscuring element for at least partially obscuring a view of wound exudate absorbed by the absorbent layer in use.

The obscuring element may be partially translucent.

The obscuring element may be a masking layer.

The non-negative pressure wound dressing may further comprise a region in or adjacent the obscuring element for allowing viewing of the absorbent layer. For example, the obscuring element layer may be provided over a central region of the absorbent layer and not over a border region of the absorbent layer. In some embodiments, the obscuring element is of hydrophilic material or is coated with a hydrophilic material.

The obscuring element may comprise a three-dimensional knitted spacer fabric. The spacer fabric is known in the art and may include a knitted spacer fabric layer.

The obscuring element may further comprise an indicator for indicating the need to change the dressing.

In some embodiments, the obscuring element is provided as a layer at least partially over the absorbent layer, further from a wound site than the absorbent layer in use.

The non-negative pressure wound dressing may further comprise a plurality of openings in the obscuring element for allowing fluid to move therethrough. The obscuring element may comprise, or may be coated with, a material having size-exclusion properties for selectively permitting or preventing passage of molecules of a predetermined size or weight.

The obscuring element may be configured to at least partially mask light radiation having wavelength of 600 nm and less.

The obscuring element may be configured to reduce light absorption by 50% or more.

The obscuring element may be configured to yield a CIE L* value of 50 or more, and optionally 70 or more. In some embodiments, the obscuring element may be configured to yield a CIE L* value of 70 or more.

In some embodiments, the non-negative pressure wound dressing may further comprise at least one of a wound contact layer, a foam layer, an odor control element, a pressure-resistant layer and a cover layer.

In some embodiments, the cover layer is present, and the cover layer is a translucent film Typically, the translucent film has a moisture vapour permeability of 500 g/m2/24 hours or more.

The translucent film may be a bacterial bather.

In some embodiments, the non-negative pressure wound dressing as disclosed herein comprises the wound contact layer and the absorbent layer overlies the wound contact layer. The wound contact layer carries an adhesive portion for forming a substantially fluid tight seal over the wound site.

The non-negative pressure wound dressing as disclosed herein may comprise the obscuring element and the absorbent layer being provided as a single layer.

In some embodiments, the non-negative pressure wound dressing disclosed herein comprises the foam layer, and the obscuring element is of a material comprising components that may be displaced or broken by movement of the obscuring element.

In some embodiments, the non-negative pressure wound dressing comprises an odor control element, and in another embodiment the dressing does not include an odor control element. When present, the odor control element may be dispersed within or adjacent the absorbent layer or the obscuring element. Alternatively, when present the odor control element may be provided as a layer sandwiched between the foam layer and the absorbent layer.

In some embodiments, the disclosed technology for a non-negative pressure wound dressing comprises a method of manufacturing a wound dressing, comprising: providing an absorbent layer for absorbing wound exudate; and providing an obscuring element for at least partially obscuring a view of wound exudate absorbed by the absorbent layer in use.

In some embodiments, the non-negative pressure wound dressing is may be suitable for providing protection at a wound site, comprising: an absorbent layer for absorbing wound exudate; and a shielding layer provided over the absorbent layer, and further from a wound-facing side of the wound dressing than the absorbent layer. The shielding layer may be provided directly over the absorbent layer. In some embodiments, the shielding layer comprises a three-dimensional spacer fabric layer.

The shielding layer increases the area over which a pressure applied to the dressing is transferred by 25% or more or the initial area of application. For example the shielding layer increases the area over which a pressure applied to the dressing is transferred by 50% or more, and optionally by 100% or more, and optionally by 200% or more.

The shielding layer may comprise 2 or more sub-layers, wherein a first sub-layer comprises through holes and a further sub-layer comprises through holes and the through holes of the first sub-layer are offset from the through holes of the further sub-layer.

The non-negative pressure wound dressing as disclosed herein may further comprise a permeable cover layer for allowing the transmission of gas and vapour therethrough, the cover layer provided over the shielding layer, wherein through holes of the cover layer are offset from through holes of the shielding layer.

The non-negative pressure wound dressing may be suitable for treatment of pressure ulcers.

A more detailed description of the non-negative pressure dressing disclosed hereinabove is provided in WO2013007973, the entirety of which is hereby incorporated by reference.

In some embodiments, the non-negative pressure wound dressing may be a multi-layered wound dressing comprising: a fibrous absorbent layer for absorbing exudate from a wound site; and a support layer configured to reduce shrinkage of at least a portion of the wound dressing.

In some embodiments, the multi-layered wound dressing disclosed herein, further comprises a liquid impermeable film layer, wherein the support layer is located between the absorbent layer and the film layer.

The support layer disclosed herein may comprise a net. The net may comprise a geometric structure having a plurality of substantially geometric apertures extending therethrough. The geometric structure may for example comprise a plurality of bosses substantially evenly spaced and joined by polymer strands to form the substantially geometric apertures between the polymer strands.

The net may be formed from high density polyethylene.

The apertures may have an area from 0.005 to 0.32 mm2.

The support layer may have a tensile strength from 0.05 to 0.06 Nm.

The support layer may have a thickness of from 50 to 150 µm.

In some embodiments, the support layer is located directly adjacent the absorbent layer. Typically, the support layer is bonded to fibers in a top surface of the absorbent layer. The support layer may further comprise a bonding layer, wherein the support layer is heat laminated to the fibers in the absorbent layer via the bonding layer. The bonding layer may comprise a low melting point adhesive such as ethylene-vinyl acetate adhesive.

In some embodiments, the multi-layered wound dressing disclosed herein further comprises an adhesive layer attaching the film layer to the support layer.

In some embodiments, the multi-layered wound dressing disclosed herein further comprises a wound contact layer located adjacent the absorbent layer for positioning adjacent a wound. The multi-layered wound dressing may further comprise a fluid transport layer between the wound contact layer and the absorbent layer for transporting exudate away from a wound into the absorbent layer.

A more detailed description of the multi-layered wound dressing disclosed hereinabove is provided in GB patent application filed on 28 Oct. 2016 with application number GB1618298.2, the entirety of which is hereby incorporated by reference.

In some embodiments, the disclosed technology may be incorporated in a wound dressing comprising a vertically lapped material comprising: a first layer of an absorbing layer of material, and a second layer of material, wherein the first layer being constructed from at least one layer of non-woven textile fibers, the non-woven textile fibers being folded into a plurality of folds to form a pleated structure. In some embodiments, the wound dressing further comprises a second layer of material that is temporarily or permanently connected to the first layer of material.

Typically the vertically lapped material has been slitted.

In some embodiments, the first layer has a pleated structure having a depth determined by the depth of pleats or by the slitting width. The first layer of material may be a moldable, lightweight, fiber-based material, blend of material or composition layer.

The first layer of material may comprise one or more of manufactured fibers from synthetic, natural or inorganic polymers, natural fibers of a cellulosic, proteinaceous or mineral source.

The wound dressing may comprise two or more layers of the absorbing layer of material vertically lapped material stacked one on top of the other, wherein the two or more layers have the same or different densities or composition.

The wound dressing may in some embodiments comprise only one layer of the absorbing layer of material vertically lapped material.

The absorbing layer of material is a blend of natural or synthetic, organic or inorganic fibers, and binder fibers, or bicomponent fibers typically PET with a low melt temperature PET coating to soften at specified temperatures and to act as a bonding agent in the overall blend.

In some embodiments, the absorbing layer of material may be a blend of 5 to 95% thermoplastic polymer, and 5 to 95 wt % of a cellulose or derivative thereof.

In some embodiments, the wound dressing disclosed herein has a second layer comprises a foam or a dressing fixative.

The foam may be a polyurethane foam. The polyurethane foam may have an open or closed pore structure.

The dressing fixative may include bandages, tape, gauze, or backing layer.

In some embodiments, the wound dressing as disclosed herein comprises the absorbing layer of material connected directly to a second layer by lamination or by an adhesive, and the second layer is connected to a dressing fixative layer. The adhesive may be an acrylic adhesive, or a silicone adhesive.

In some embodiments, the wound dressing as disclosed herein further comprises layer of a superabsorbent fiber, or a viscose fiber or a polyester fiber.

In some embodiments, the wound dressing as disclosed herein further comprises a backing layer. The backing layer may be a transparent or opaque film. Typically the backing layer comprises a polyurethane film (typically a transparent polyurethane film).

A more detailed description of the multi-layered wound dressing disclosed hereinabove is provided in GB patent applications filed on 12 Dec. 2016 with application number GB1621057.7; and 22 Jun. 2017 with application number GB1709987.0, the entirety of each of which is hereby incorporated by reference.

In some embodiments, the non-negative pressure wound dressing may comprise an absorbent component for a wound dressing, the component comprising a wound contacting layer comprising gel forming fibers bound to a foam layer, wherein the foam layer is bound directly to the wound contact layer by an adhesive, polymer based melt layer, by flame lamination or by ultrasound.

The absorbent component may be in a sheet form.

The wound contacting layer may comprise a layer of woven or non-woven or knitted gel forming fibers.

The foam layer may be an open cell foam, or closed cell foam, typically an open cell foam. The foam layer is a hydrophilic foam.

The wound dressing may comprise the component that forms an island in direct contact with the wound surrounded by periphery of adhesive that adheres the dressing to the wound. The adhesive may be a silicone or acrylic adhesive, typically a silicone adhesive.

The wound dressing may be covered by a film layer on the surface of the dressing furthest from the wound.

A more detailed description of the wound dressing of this type hereinabove is provided in EP2498829, the entirety of which is hereby incorporated by reference.

In some embodiments, the non-negative pressure wound dressing may comprise a multi layered wound dressing for use on wounds producing high levels of exudate, characterized in that the dressing comprising: a transmission layer having an MVTR of at least 300 µm2/24 hours, an absorbent core comprising gel forming fibers capable of absorbing and retaining exudate, a wound contacting layer comprising gel forming fibers which transmits exudate to the absorbent core and a keying layer positioned on the absorbent core, the absorbent core and wound contacting layer limiting the lateral spread of exudate in the dressing to the region of the wound.

The wound dressing may be capable of handling at least 6 g (or 8 g and 15 g) of fluid per 10 cm2 of dressing in 24 hours.

The wound dressing may comprise gel forming fibers that are chemically modified cellulosic fibers in the form of a fabric. The fibers may include carboxymethylated cellulose fibers, typically sodium carboxymethylcellulose fiber.

The wound dressing may comprise a wound contact layer with a lateral wicking rate from 5 mm per minute to 40 mm per minute. The wound contact layer may have a fiber density between 25 gm2 and 55 gm2, such as 35 gm2.

The absorbent core may have an absorbency of exudate of at least 10 g/g, and typically a rate of lateral wicking of less the 20 mm per minute.

The absorbent core may have a blend in the range of up to 25% cellulosic fibers by weight and 75% to 100% gel forming fibers by weight.

Alternatively, the absorbent core may have a blend in the range of up to 50% cellulosic fibers by weight and 50% to 100% gel forming fibers by weight. For example the blend is in the range of 50% cellulosic fibers by weight and 50% gel forming fibers by weight.

The fiber density in the absorbent core may be between 150 gm2 and 250 gm2, or about 200 gm2.

The wound dressing when wet may have shrinkage that is less than 25% or less than 15% of its original size/dimension.

The wound dressing may comprise a transmission layer and the layer is a foam. The transmission layer may be a polyurethane foam laminated to a polyurethane film.

The wound dressing may comprise one or more layers selected from the group comprising a soluble medicated film layer; an odor-absorbing layer; a spreading layer and an additional adhesive layer.

The wound dressing may be 2 mm and 4 mm thick.

The wound dressing may be characterized in that the keying layer bonds the absorbent core to a neighboring layer. In some embodiments, the keying layer may be positioned on either the wound facing side of the absorbent core or the non-wound facing side of the absorbent core. In some embodiments, the keying layer is positioned between the absorbent core and the wound contact layer. The keying layer is a polyamide web.

A more detailed description of the wound dressing of this type hereinabove is provided in EP1718257, the entirety of which is hereby incorporated by reference.

In some embodiments, the non-negative pressure wound dressing may be a compression bandage. Compression bandages are known for use in the treatment of oedema and other venous and lymphatic disorders, e.g., of the lower limbs.

A compression bandage systems typically employ multiple layers including a padding layer between the skin and the compression layer or layers. The compression bandage may be useful for wounds such as handling venous leg ulcers.

The compression bandage in some embodiments may comprise a bandage system comprising an inner skin facing layer and an elastic outer layer, the inner layer comprising a first ply of foam and a second ply of an absorbent nonwoven web, the inner layer and outer layer being sufficiently elongated so as to be capable of being wound about a patient's limb. A compression bandage of this type is disclosed in WO99/58090, the entirety of which is hereby incorporated by reference.

In some embodiments, the compression bandage system comprises: a) an inner skin facing, elongated, elastic bandage comprising: (i) an elongated, elastic substrate, and (ii) an elongated layer of foam, said foam layer being affixed to a face of said substrate and extending 33% or more across said face of substrate in transverse direction and 67% or more across said face of substrate in longitudinal direction; and b) an outer, elongated, self-adhering elastic bandage; said bandage having a compressive force when extended; wherein, in use, said foam layer of the inner bandage faces the skin and the outer bandage overlies the inner bandage. A compression bandage of this type is disclosed in WO2006/110527, the entirety of which is hereby incorporated by reference.

In some embodiments other compression bandage systems such as those disclosed in U.S. Pat. No. 6,759,566 and US 2002/0099318, the entirety of each of which is hereby incorporated by reference.

Negative Pressure Wound Dressing

In some embodiments, treatment of such wounds can be performed using negative pressure wound therapy, wherein a reduced or negative pressure can be applied to the wound to facilitate and promote healing of the wound. It will also be appreciated that the wound dressing and methods as disclosed herein may be applied to other parts of the body, and are not necessarily limited to treatment of wounds.

It will be understood that embodiments of the present disclosure are generally applicable to use in topical negative pressure ("TNP") therapy systems. Briefly, negative pressure wound therapy assists in the closure and healing of many forms of "hard to heal" wounds by reducing tissue oedema; encouraging blood flow and granular tissue formation; removing excess exudate and may reduce bacterial load (and thus infection risk). In addition, the therapy allows for less disturbance of a wound leading to more rapid healing. TNP therapy systems may also assist on the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

Negative pressure therapy can be used for the treatment of open or chronic wounds that are too large to spontaneously close or otherwise fail to heal by means of applying negative pressure to the site of the wound. Topical negative pressure (TNP) therapy or negative pressure wound therapy (NPWT) involves placing a cover that is impermeable or semi-permeable to fluids over the wound, using various means to seal the cover to the tissue of the patient surrounding the wound, and connecting a source of negative pressure (such as a vacuum pump) to the cover in a manner so that negative pressure is created and maintained under the cover. It is believed that such negative pressures promote wound healing by facilitating the formation of granulation tissue at the wound site and assisting the body's normal inflammatory process while simultaneously removing excess fluid, which may contain adverse cytokines or bacteria.

Some of the dressings used in NPWT can include many different types of materials and layers, for example, gauze, pads, foam pads or multi-layer wound dressings. One example of a multi-layer wound dressing is the PICO dressing, available from Smith & Nephew, includes a wound contact layer and a superabsorbent layer beneath a backing layer to provide a canister-less system for treating a wound with NPWT. The wound dressing may be sealed to a suction port providing connection to a length of tubing, which may be used to pump fluid out of the dressing or to transmit negative pressure from a pump to the wound dressing. Additionally, RENASYS-F, RENASYS-G, RENASYS-AB, and RENASYS-F/AB, available from Smith & Nephew, are additional examples of NPWT wound dressings and systems. Another example of a multi-layer wound dressing is the ALLEVYN Life dressing, available from Smith & Nephew, which includes a moist wound environment dressing that is used to treat the wound without the use of negative pressure.

As is used herein, reduced or negative pressure levels, such as −X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of −X mmHg reflects absolute pressure that is X mmHg below 760 mmHg or, in other words, an absolute pressure of (760−X) mmHg In addition, negative pressure that is "less" or "smaller" than X mmHg corresponds to pressure that is closer to atmospheric pressure (such as, −40 mmHg is less than −60 mmHg). Negative pressure that is "more" or "greater" than −X mmHg corresponds to pressure that is further from atmospheric pressure (such as, −80 mmHg is more than −60 mmHg). In some embodiments, local ambient atmospheric pressure is used as a reference point, and such local atmospheric pressure may not necessarily be, for example, 760 mmHG.

The negative pressure range for some embodiments of the present disclosure can be approximately −80 mmHg, or between about −20 mmHg and −200 mmHg Note that these pressures are relative to normal ambient atmospheric pressure, which can be 760 mmHg Thus, −200 mmHg would be about 560 mmHg in practical terms. In some embodiments, the pressure range can be between about −40 mmHg and −150 mmHg. Alternatively a pressure range of up to −75 mmHg, up to −80 mmHg or over −80 mmHg can be used. Also in other embodiments a pressure range of below −75 mmHg can be used. Alternatively, a pressure range of over approximately −100 mmHg, or even −150 mmHg, can be supplied by the negative pressure apparatus.

In some embodiments of wound closure devices described herein, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via embodiments of the wound closure devices. In some embodiments, negative pressure may be varied over time for example using a sinusoidal wave, square wave, or in synchronization with one or more patient physiological indices (such as, heartbeat). Examples of such applications where additional disclosure relating to the preceding may be found include U.S. Pat. No. 8,235,955, titled "Wound treatment apparatus and method," issued on Aug. 7, 2012; and U.S. Pat. No. 7,753,894, titled "Wound cleansing apparatus with stress," issued Jul. 13, 2010. The disclosures of both of these patents are hereby incorporated by reference in their entirety.

Embodiments of the wound dressings, wound dressing components, wound treatment apparatuses and methods described herein may also be used in combination or in addition to those described in International Application No. PCT/IB2013/001469, filed May 22, 2013, published as WO 2013/175306 A2 on Nov. 28, 2013, titled "APPARATUSES AND METHODS FOR NEGATIVE PRESSURE WOUND THERAPY," U.S. patent application Ser. No. 14/418,908, filed Jan. 30, 2015, published as US 2015/0190286 A1 on Jul. 9, 2015, titled "WOUND DRESSING AND METHOD OF TREATMENT," the disclosures of which are hereby incorporated by reference in their entireties. Embodiments of the wound dressings, wound dressing components, wound treatment apparatuses and methods described herein may also be used in combination or in addition to those described in U.S. patent application Ser. No. 13/092,042, filed Apr. 21, 2011, published as US2011/0282309, titled "WOUND DRESSING AND METHOD OF USE," and U.S. patent application Ser. No. 14/715,527, filed May 18, 2015, published as US2016/0339158 A1 on Nov. 24, 2016, titled "FLUIDIC CONNECTOR FOR NEGATIVE PRESSURE WOUND THERAPY," the disclosure of each of which is hereby incorporated by reference in its entirety, including further details relating to embodiments of wound dressings, the wound dressing components and principles, and the materials used for the wound dressings.

Additionally, some embodiments related to TNP wound treatment comprising a wound dressing in combination with a pump or associated electronics described herein may also be used in combination or in addition to those described in International Application PCT/EP2016/059329 filed Apr. 26, 2016, published as WO 2016/174048 on Nov. 3, 2016, entitled "REDUCED PRESSURE APPARATUS AND METHODS," the disclosure of which is hereby incorporated by reference in its entirety.

In some embodiments of wound closure devices described herein, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via embodiments of the wound closure devices. Further, there may be additional effects on tissues in close proximity to the filler, for example, the tissue is under compression due to the reactive force of the elastic filler pressing on the tissue. Such compression may result in in local hypoxia due to occlusion of the blood vessels. In the wider peripheral tissue, this expansion may lead to blood vessel expansion. Further details are provided in "NPWT settings and dressing choices made easy" by Malmsjo and Borgquist, published in Wounds International in May 2010, hereby incorporated by reference in its entirety. For example, in a wound that is not at risk for ischemia, the increased and decreased blood flow caused by pressure from the wound dressing is likely advantageous for wound healing. The increase in blood flow may improve oxygen and nutrient supply to the tissue, and improve penetration of antibiotics and the removal of waste. Additionally, the reduction in blood flow may stimulate angiogenesis, thereby promoting granulation tissue formation.

Wound Healing

One of skill in the art will understand that the embodiments described herein, particularly with reference to Eulerian Video Magnification (EVM), are not merely applicable to situations involving NPWT. Rather, such embodiments may be broadly applicable to situations that do not necessarily require NPWT, such as evaluating intact tissue or providing additional treatments to wounds.

Wounds may be generally categorized as open or closed, often depending upon how the wound is caused. As described above, the techniques may be applied to both open and to closed wounds, depending on the particulars of the embodiment. Open wounds may be caused by a variety of events, including: incisions, lacerations, abrasions, punctures, penetration, amputation, and other means. Closed wounds may be caused by damage to a blood vessel resulting in formation of a hematoma, and/or by internal injuries caused by crushing. Further, wounds may involve various layers of tissue, for example, shallower wounds may only involve the topmost layers of the skin, while deeper wounds may involve underlying subcutaneous tissue layers such as the hypodermis, including underlying connective tissues and fatty layers. In certain embodiments, wounds may even encompass underlying internal organs, deep beneath the skin. Certain wounds, such as those caused by pressure injuries, may start to occur within the deeper tissue layers without become evident on the surface of the skin until much later.

In addition to NPWT treatments described above, wounds may be treated by a wide variety of techniques and materials. For example, wounds may be treated by debridement to remove dead and/or necrotic tissue. Wounds may be treated with a with various type of dressings, including dry and wet dressings, chemically-impregnated dressings, foam dressing, hydrogel dressings, hydrocolloid dressings, film dressings, and other suitable dressings. Wounds may further be treated with bioactive molecules such as antimicrobials, growth factors, anti-inflammatories, analgesics and other suitable treatments. Such treatments may be incorporated into the aforementioned dressings.

Further details regarding wounds and wound treatment, in particular wounds caused by pressure injuries may be found in the article "Pressure Injuries (Pressure Ulcers) and Wound Care" by Kirman et al, published in Medscape March 2017, and hereby incorporated by reference in its entirety. For example, the most common candidates for pressure ulcers include: elderly persons, persons who are chronically ill (such as those with cancer, stroke, or diabetes), persons who are immobile (e.g, as a consequence of fracture, arthritis, or pain), persons who are weak or debilitated, patients with altered mental status (e.g., from the effects of narcotics, anesthesia, or coma), and/or persons with decreased sensation or paralysis. Potential secondary factors include: illness or debilitation that increases pressure ulcer formation, fever (increases metabolic demands), predisposing ischemia, diaphoresis which promotes skin maceration, incontinence which causes skin irritation and contamination, edema, jaundice, pruritus, and xerosis (dry skin). Additionally, prevention of pressure ulcer injuries may include: scheduled body turning, appropriate bed positioning, protection of bony prominences, skin care, control of spascity and prevention of contractures, use of support surfaces/specialty beds, nutritional support, and maintenance of current levels of activity, mobility and range of motion.

Negative Pressure System

FIG. 1 illustrates an embodiment of a negative or reduced pressure wound treatment (or TNP) system 100 comprising a wound filler 130 placed inside a wound cavity 110, the wound cavity sealed by a wound cover 120. The wound filler 130 in combination with the wound cover 120 can be referred to as wound dressing. A single or multi lumen tube or conduit 140 is connected the wound cover 120 with a pump assembly 150 configured to supply reduced pressure. The wound cover 120 can be in fluidic communication with the wound cavity 110. In any of the system embodiments disclosed herein, as in the embodiment illustrated in FIG. 1, the pump assembly can be a canisterless pump assembly (meaning that exudate is collected in the wound dressing or is transferred via tube 140 for collection to another location). However, any of the pump assembly embodiments disclosed herein can be configured to include or support a canister. Additionally, in any of the system embodiments disclosed herein, any of the pump assembly embodiments can be mounted to or supported by the dressing, or adjacent to the dressing.

The wound filler 130 can be any suitable type, such as hydrophilic or hydrophobic foam, gauze, inflatable bag, and so on. The wound filler 130 can be conformable to the wound cavity 110 such that it substantially fills the cavity. The wound cover 120 can provide a substantially fluid impermeable seal over the wound cavity 110. The wound cover 120 can have a top side and a bottom side, and the bottom side adhesively (or in any other suitable manner) seals with wound cavity 110. The conduit 140 or lumen or any other conduit or lumen disclosed herein can be formed from polyurethane, PVC, nylon, polyethylene, silicone, or any other suitable material.

Some embodiments of the wound cover 120 can have a port (not shown) configured to receive an end of the conduit 140. For example, the port can be Renays Soft Port available from Smith & Nephew. In other embodiments, the conduit 140 can otherwise pass through or under the wound cover 120 to supply reduced pressure to the wound cavity 110 so as to maintain a target or desired level of reduced pressure in the wound cavity. The conduit 140 can be any suitable article configured to provide at least a substantially sealed fluid flow pathway between the pump assembly 150 and the wound cover 120, so as to supply the reduced pressure provided by the pump assembly 150 to wound cavity 110.

The wound cover 120 and the wound filler 130 can be provided as a single article or an integrated single unit. In some embodiments, no wound filler is provided and the wound cover by itself may be considered the wound dressing. The wound dressing may then be connected, via the conduit 140, to a source of negative pressure, such as the pump assembly 150. The pump assembly 150 can be miniaturized and portable, although larger conventional pumps such can also be used.

The wound cover 120 can be located over a wound site to be treated. The wound cover 120 can form a substantially sealed cavity or enclosure over the wound site. In some embodiments, the wound cover 120 can be configured to have a film having a high water vapor permeability to enable the evaporation of surplus fluid, and can have a superabsorbing material contained therein to safely absorb wound exudate. It will be appreciated that throughout this specification reference is made to a wound. In this sense it is to be understood that the term wound is to be broadly construed and encompasses open and closed wounds in which skin is torn, cut or punctured or where trauma causes a contusion, or any other surficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, acute wounds, chronic wounds, surgical incisions and other incisions, subacute and dehisced wounds, traumatic wounds, flaps and skin grafts, lacerations, abrasions, contusions, burns, diabetic ulcers, pressure ulcers, stoma, surgical wounds, trauma and venous ulcers or the like. The components of the TNP system described herein can be particularly suited for incisional wounds that exude a small amount of wound exudate.

Some embodiments of the system are designed to operate without the use of an exudate canister. Some embodiments can be configured to support an exudate canister. In some embodiments, configuring the pump assembly 150 and tubing 140 so that the tubing 140 can be quickly and easily removed from the pump assembly 150 can facilitate or improve the process of dressing or pump changes, if necessary. Any of the pump embodiments disclosed herein can be configured to have any suitable connection between the tubing and the pump.

The pump assembly 150 can be configured to deliver negative pressure of approximately −80 mmHg, or between about −20 mmHg and 200 mmHg in some implementations. Note that these pressures are relative to normal ambient atmospheric pressure thus, −200 mmHg would be about 560 mmHg in practical terms. The pressure range can be between about −40 mmHg and −150 mmHg. Alternatively a pressure range of up to −75 mmHg, up to −80 mmHg or over −80 mmHg can be used. Also a pressure range of below −75 mmHg can be used. Alternatively a pressure range of over approximately −100 mmHg, or even 150 mmHg, can be supplied by the pump assembly 150.

In operation, the wound filler 130 is inserted into the wound cavity 110 and wound cover 120 is placed so as to seal the wound cavity 110. The pump assembly 150 provides a source of a negative pressure to the wound cover 120, which is transmitted to the wound cavity 110 via the wound filler 130. Fluid (e.g., wound exudate) is drawn through the conduit 140, and can be stored in a canister. In some embodiments, fluid is absorbed by the wound filler 130 or one or more absorbent layers (not shown).

Wound dressings that may be utilized with the pump assembly and other embodiments of the present application include Renasys-F, Renasys-G, Renasys AB, and Pico Dressings available from Smith & Nephew. Further description of such wound dressings and other components of a negative pressure wound therapy system that may be used with the pump assembly and other embodiments of the present application are found in U.S. Patent Publication Nos. 2011/0213287, 2011/0282309, 2012/0116334, 2012/0136325, and 2013/0110058, which are incorporated by reference in their entirety. In other embodiments, other suitable wound dressings can be utilized.

Pump Assembly and Canister

Figure 2A:
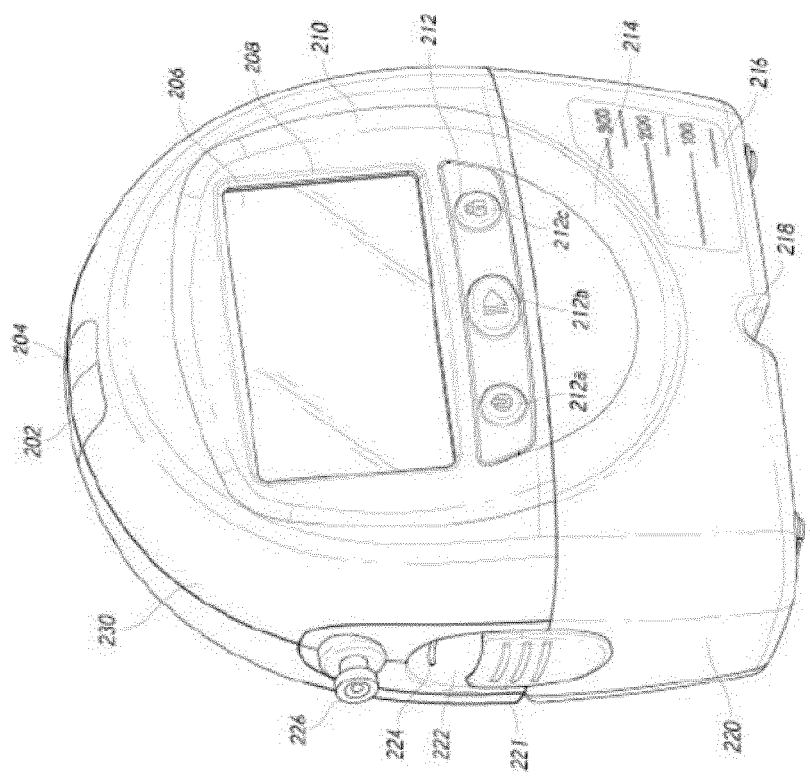
FIGS. 2A, 2B, and 2C illustrate a pump assembly and canister according to some embodiments.

FIG. 2A illustrates a front view of a pump assembly 230 and canister 220 according to some embodiments. As is illustrated, the pump assembly 230 and the canister are connected, thereby forming a negative pressure wound therapy device. The pump assembly 230 can be similar to or the same as the pump assembly 150 in some embodiments.

The pump assembly 230 includes one or more indicators, such as visual indicator 202 configured to indicate alarms and visual indicator 204 configured to indicate status of the TNP system. The indicators 202 and 204 can be configured to alert a user, such as patient or medical care provider, to a variety of operating or failure conditions of the system, including alerting the user to normal or proper operating conditions, pump failure, power supplied to the pump or power failure, detection of a leak within the wound cover or flow pathway, suction blockage, or any other similar or suitable conditions or combinations thereof. The pump assembly 230 can comprise additional indicators. The pump assembly can use a single indicator or multiple indicators. Any suitable indicator can be used such as visual, audio, tactile indicator, and so on. The indicator 202 can be configured to signal alarm conditions, such as canister full, power low, conduit 140 disconnected, seal broken in the wound seal 120, and so on. The indicator 202 can be configured to display red flashing light to draw user's attention. The indicator 204 can be configured to signal status of the TNP system, such as therapy delivery is ok, leak detected, and so on. The indicator 204 can be configured to display one or more different colors of light, such as green, yellow, etc. For example, green light can be emitted when the TNP system is operating properly and yellow light can be emitted to indicate a warning.

The pump assembly 230 includes a display or screen 206 mounted in a recess 208 formed in a case of the pump assembly. The display 206 can be a touch screen display. The display 206 can support playback of audiovisual (AV) content, such as instructional videos. As explained below, the display 206 can be configured to render a number of screens or graphical user interfaces (GUIs) for configuring, controlling, and monitoring the operation of the TNP system. The pump assembly 230 comprises a gripping portion 210 formed in the case of the pump assembly. The gripping portion 210 can be configured to assist the user to hold the pump assembly 230, such as during removal of the canister 220. The canister 220 can be replaced with another canister, such as when the canister 220 has been filled with fluid.

The pump assembly 230 includes one or more keys or buttons configured to allow the user to operate and monitor the operation of the TNP system. As is illustrated, there buttons 212a, 212b, and 212c (collectively referred to as buttons 212) are included. Button 212a can be configured as a power button to turn on/off the pump assembly 230. Button 212b can be configured as a play/pause button for the delivery of negative pressure therapy. For example, pressing the button 212b can cause therapy to start, and pressing the button 212b afterward can cause therapy to pause or end. Button 212c can be configured to lock the display 206 or the buttons 212. For instance, button 212c can be pressed so that the user does not unintentionally alter the delivery of the therapy. Button 212c can be depressed to unlock the controls. In other embodiments, additional buttons can be used or one or more of the illustrated buttons 212a, 212b, or 212c can be omitted. Multiple key presses or sequences of key presses can be used to operate the pump assembly 230.

The pump assembly 230 includes one or more latch recesses 222 formed in the cover. In the illustrated embodiment, two latch recesses 222 can be formed on the sides of the pump assembly 230. The latch recesses 222 can be configured to allow attachment and detachment of the canister 220 using one or more canister latches 221. The pump assembly 230 comprises an air outlet 224 for allowing air removed from the wound cavity 110 to escape. Air entering the pump assembly can be passed through one or more suitable filters, such as antibacterial filters. This can maintain reusability of the pump assembly. The pump assembly 230 includes one or more strap mounts 226 for connecting a carry strap to the pump assembly 230 or for attaching a cradle. In the illustrated embodiment, two strap mounts 226 can be formed on the sides of the pump assembly 230. In some embodiments, various of these features are omitted or various additional features are added to the pump assembly 230.

The canister 220 is configured to hold fluid (e.g., exudate) removed from the wound cavity 110. The canister 220 includes one or more latches 221 for attaching the canister to the pump assembly 230. In the illustrated embodiment, the canister 220 comprises two latches 221 on the sides of the canister. The exterior of the canister 220 can formed from frosted plastic so that the canister is substantially opaque and the contents of the canister and substantially hidden from plain view. The canister 220 comprises a gripping portion 214 formed in a case of the canister. The gripping portion 214 can be configured to allow the user to hold the pump assembly 220, such as during removal of the canister from the apparatus 230. The canister 220 includes a substantially transparent window 216, which can also include graduations of volume. For example, the illustrated 300 mL canister 220 includes graduations of 50 mL, 100 mL, 150 mL, 200 mL, 250 mL, and 300 mL. Other embodiments of the canister can hold different volume of fluid and can include different graduation scale. For example, the canister can be an 800 mL canister. The canister 220 comprises a tubing channel 218 for connecting to the conduit 140. In some embodiments, various of these features, such as the gripping portion 214, are omitted or various additional features are added to the canister 220. Any of the disclosed canisters may include or may omit a solidifier.

Figure 2B:
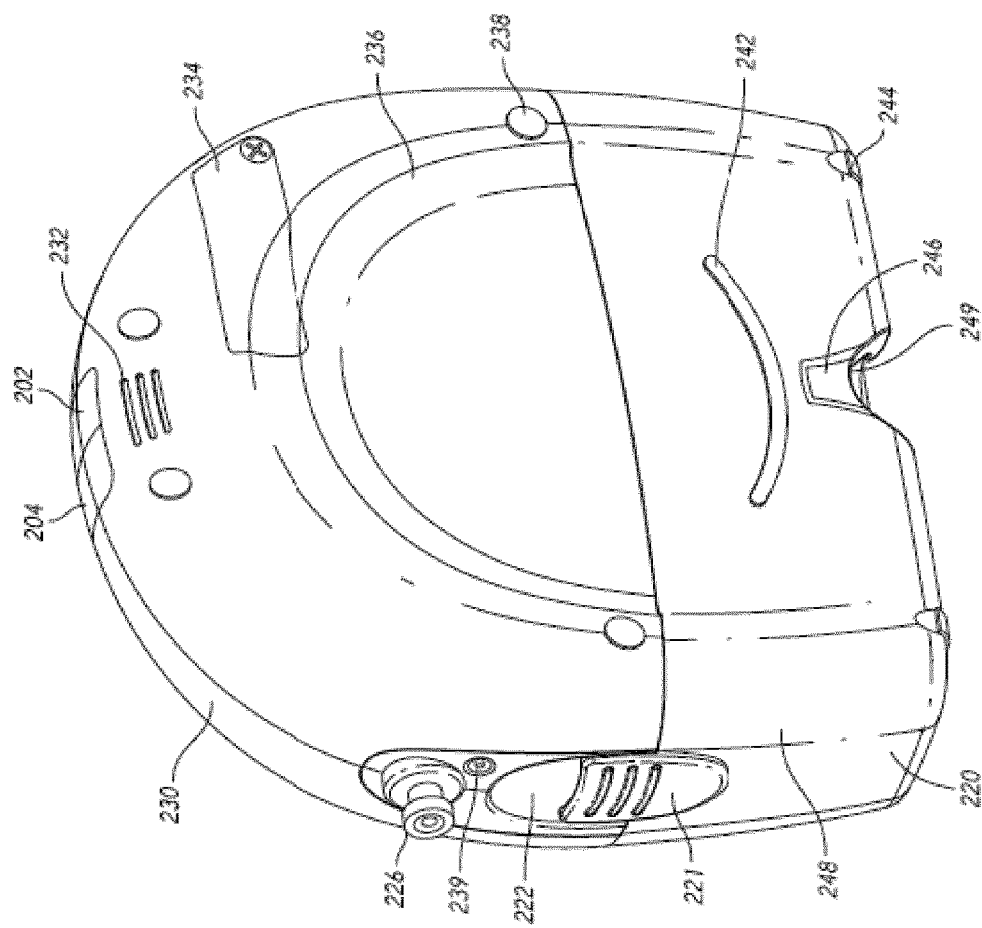

FIG. 2B illustrates a rear view of the pump assembly 230 and canister 220 according to some embodiments. The pump assembly 230 comprises a speaker port 232 for producing sound. The pump assembly 230 includes a filter access door 234 with a screw for removing the access door 234, accessing, and replacing one or more filters, such as antibacterial or odor filters. The pump assembly 230 comprises a gripping portion 236 formed in the case of the pump assembly. The gripping portion 236 can be configured to allow the user to hold the pump assembly 230, such as during removal of the canister 220. The pump assembly 230 includes one or more covers 238 configured to as screw covers or feet or protectors for placing the pump assembly 230 on a surface. The covers 230 can be formed out of rubber, silicone, or any other suitable material. The pump assembly 230 comprises a power jack 239 for charging and recharging an internal battery of the pump assembly. The power jack 239 can be a direct current (DC) jack. In some embodiments, the pump assembly can comprise a disposable power source, such as batteries, so that no power jack is needed.

The canister 220 includes one or more feet 244 for placing the canister on a surface. The feet 244 can be formed out of rubber, silicone, or any other suitable material and can be angled at a suitable angle so that the canister 220 remains stable when placed on the surface. The canister 220 comprises a tube mount relief 246 configured to allow one or more tubes to exit to the front of the device. The canister 220 includes a stand or kickstand 248 for supporting the canister when it is placed on a surface. As explained below, the kickstand 248 can pivot between an opened and closed position. In closed position, the kickstand 248 can be latched to the canister 220. In some embodiments, the kickstand 248 can be made out of opaque material, such as plastic. In other embodiments, the kickstand 248 can be made out of transparent material. The kickstand 248 includes a gripping portion 242 formed in the kickstand. The gripping portion 242 can be configured to allow the user to place the kickstand 248 in the closed position. The kickstand 248 comprises a hole 249 to allow the user to place the kickstand in the open position. The hole 249 can be sized to allow the user to extend the kickstand using a finger.

Figure 2C:
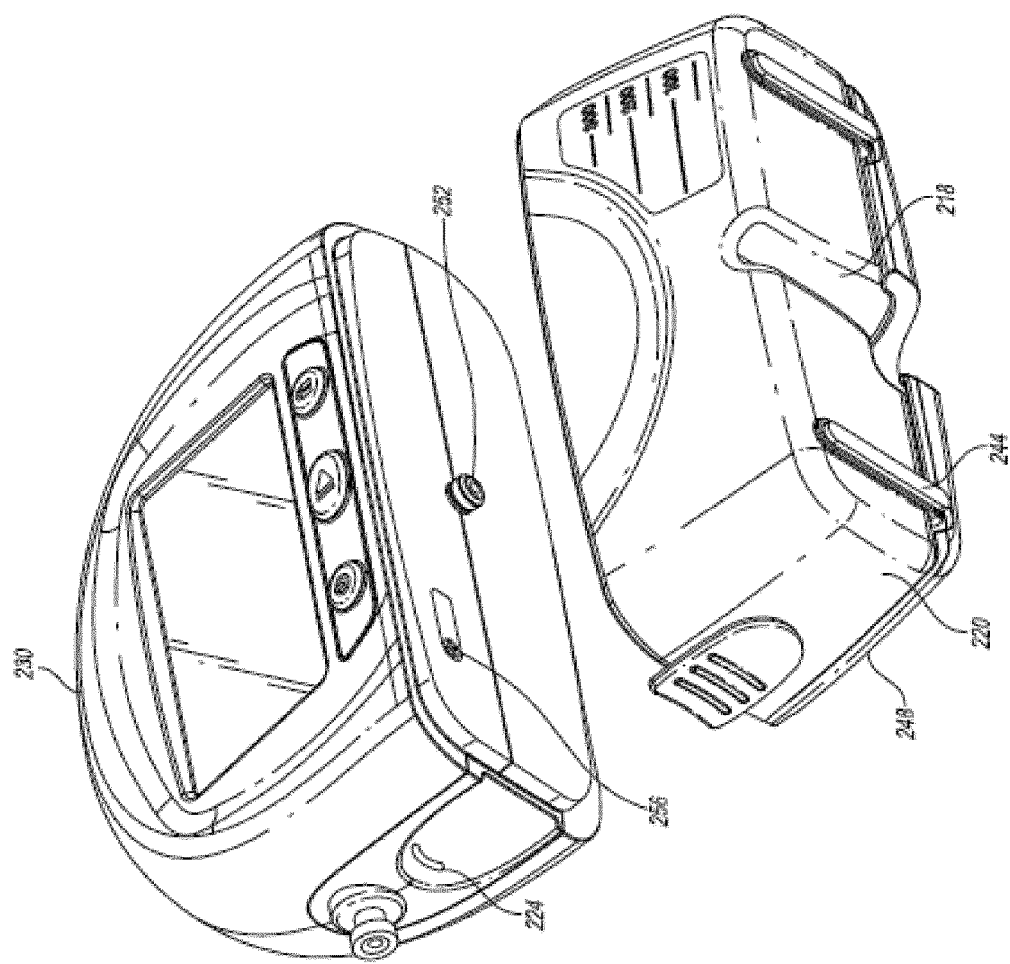

FIG. 2C illustrates a view of the pump assembly 230 separated from the canister 220 according to some embodiments. The pump assembly 230 includes a vacuum attachment, connector, or inlet 252 through which a vacuum pump communicates negative pressure to the canister 220. The pump assembly aspirates fluid, such as gas, from the wound via the inlet 252. The pump assembly 230 comprises a USB access door 256 configured to allow access to one or more USB ports. In some embodiments, the USB access door is omitted and USB ports are accessed through the door 234. The pump assembly 230 can include additional access doors configured to allow access to additional serial, parallel, or hybrid data transfer interfaces, such as SD, Compact Disc (CD), DVD, FireWire, Thunderbolt, PCI Express, and the like. In other embodiments, one or more of these additional ports are accessed through the door 234.

Eulerian Video Magnification

Novel techniques for the analysis of small changes in pixels over time have been developed using a technique called "Eulerian Video Magnification" (EVM). EVM can act to amplify these extremely small changes in pixels over time, therefore allowing detection of previously undetectable changes. For example, EVM may be applied to standard video such as those taken by an optical camera. Minute visual changes in the state of the object and/or person being videoed can then be amplified by EVM and therefore be detected. For example, EVM can detect blood flow under the skin or breathing, such as in neonatal infants. Additional details regarding EVM are provided in an article published by the Massachusetts Institute of Technology titled "Eulerian Video Magnification for Revealing Subtle Changes in the World" by Wu et al, hereby incorporated by reference in its entirety.

EVM serves to amplify subtle changes in any spatial location in a video (such as a pixel) over time. Such subtle changes may not be visible to the naked eye, therefore EVM allows for the detection of minute phenomena undetectable under normal viewing and monitoring. Such video can be collected via any suitable means and is not simply limited to video collected within the visible light spectra. For example, video may be collected via: camera, charge-coupled devices (CCDs), oxygen saturation (spO2) detector, magnetic resonance imaging, x-ray imaging, infrared imaging or any form of video data collection over time. The amplified change in a pixel value can be the result of changes due to variations in color, motion, or any other suitable change depending upon the type of video. For example, video of spO2 measurements in a particular area could output as a value, such as a color, therefore EVM applied to such a video could detect subtle changes in spO2. As described above, additional details regarding EVM are provided in an article published by the Massachusetts Institute of Technology titled "Eulerian Video Magnification for Revealing Subtle Changes in the World" by Wu et al.

Figure 3:
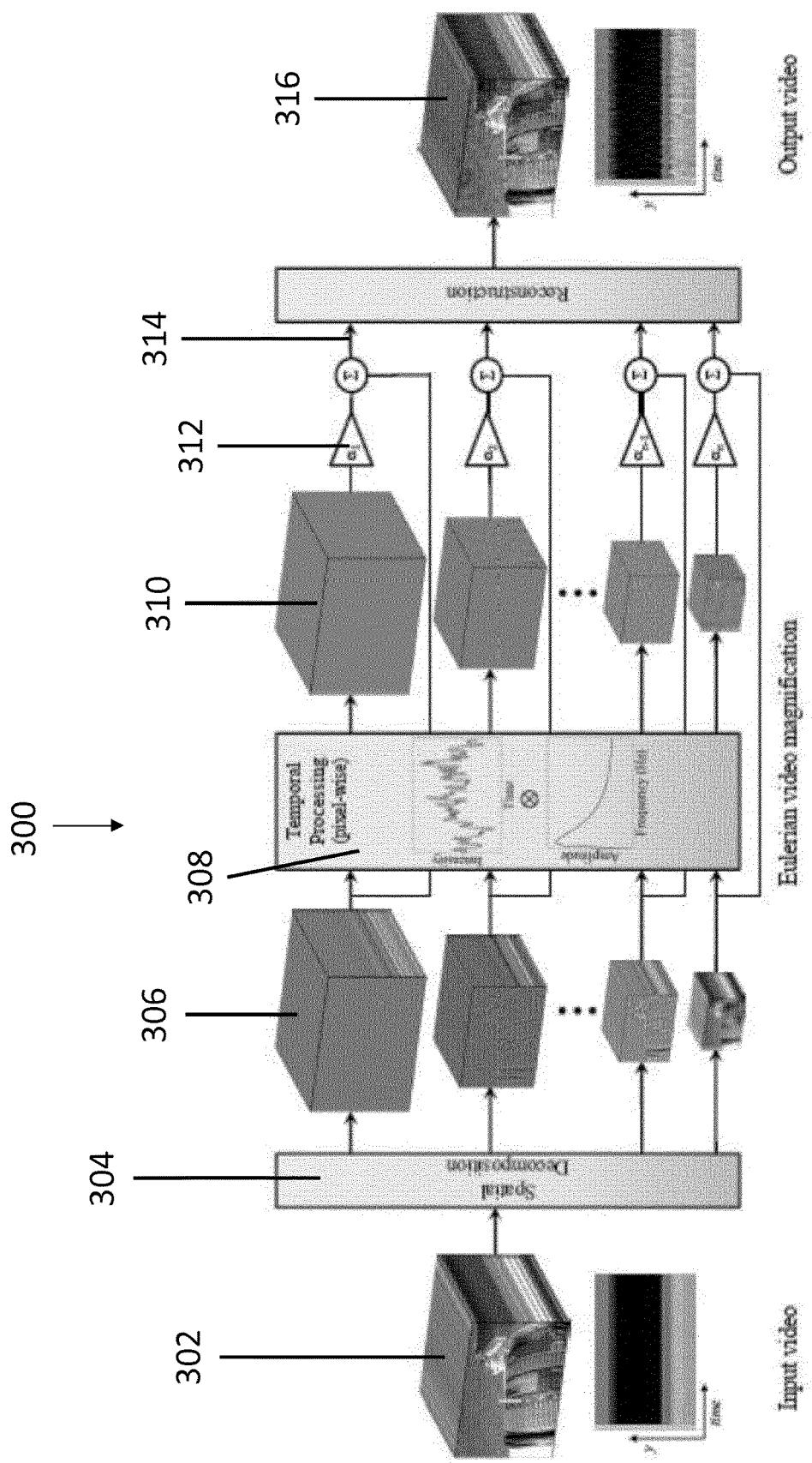
FIG. 3 illustrates an embodiment of a process for video amplification known as Eulerian Video Magnification.

As described by Wu et al, spatial and temporal processing can be used to emphasize subtle temporal changes in a video. An embodiment of this process is illustrated in FIG. 3. In brief, the EVM system 300 first decomposes 304 the input video sequence 302 into different spatial frequency bands 306, and applies the same temporal filter to all bands 308. The filtered spatial bands 310 are then amplified by a given factor α 312, added back to the original signal 314, and collapsed to generate the output video 316.

As described by Wu, first, the video sequence is decomposed into different spatial frequency bands. These bands might be magnified differently because (a) they might exhibit different signal-to-noise ratios or (b) they might contain spatial frequencies for which the linear approximation described later for motion magnification does not hold. In the latter case, amplification for these bands may be reduced to suppress artifacts. When the goal of spatial processing is simply to increase the temporal signal-to-noise ratio by pooling multiple pixels, the frames of the video may be subjected to a spatially low-pass filter and down sampled for computational efficiency. In the general case, however, a full Laplacian pyramid [Burt and Adelson 1983] may be performed, followed by temporal processing on each spatial band. The time series corresponding to the value of a pixel in a frequency band may be considered and a bandpass filter may be applied to extract the frequency bands of interest. For example, we might select frequencies within 0.4-4 Hz, corresponding to 24-240 beats per minute, if we wish to magnify a pulse. If we are able to extract the pulse rate, we can use a narrow band around that value. The temporal processing is uniform for all spatial levels, and for all pixels within each level. We then multiply the extracted band-passed signal by a magnification factor. This factor can be specified by the user, and may be attenuated automatically according to guidelines described below. Possible temporal filters are also discussed below. Next, we add the magnified signal to the original and collapse the spatial pyramid to obtain the final output. Since natural videos are spatially and temporally smooth, and since our filtering is performed uniformly over the pixels, our method implicitly maintains spatiotemporal coherency of the results.

To explain the relationship between temporal processing and motion magnification, we consider the simple case of a 1D signal undergoing translational motion. This analysis generalizes directly to locally-translational motion in 2D. Let I(x; t) denote the image intensity at position x and time t. Since the image undergoes translational motion, we can express the observed intensities with respect to a displacement function δ(t), such that I(x; t)=f(x+δ(t)) and I(x; 0)=f(x). The goal of motion magnification is to synthesize the signal Î(x,t)=f(x+(1+α)δ(t)) for some amplification factor α.

Assuming the image can be approximated by a first-order Taylor series expansion, we write the image at time t, $f(x+\delta(t))$ in a first-order Taylor expansion about x, as $$I(x, t) \approx f(x) + \delta(t)\frac{\partial f(x)}{\partial x}.$$

Let B(x; t) be the result of applying a broadband temporal bandpass filter to I(x; t) at every position x (picking out everything except f(x) in the above equation). For now, let us assume the motion signal, (t), is within the passband of the temporal bandpass filter (we will relax that assumption later). Then we have $$B(x, t) = \delta(t)\frac{\partial f(x)}{\partial x}.$$

In our process, we then amplify that bandpass signal by and add it back to I(x; t), resulting in the processed signal $$\tilde{I}(x,t)=I(x,t)+\alpha B(x,t).$$

Combining the previous equations, we now have $$\tilde{I}(x, t) \approx f(x) + (1+\alpha)\delta(t)\frac{\partial f(x)}{\partial x}.$$

Assuming the first-order Taylor expansion holds for the amplified larger perturbation, $(1+\alpha)\delta(t)$, we can relate the amplification of the temporally bandpassed signal to motion magnification. The processed output is simply $$\tilde{I}(x,t) \approx f(x+(1+\alpha)\delta(t)).$$

This shows that the processing magnifies motions—the spatial displacement δ(t) of the local image f(x) at time t, has been amplified to a magnitude of (1+α). For a low frequency cosine wave and a relatively small displacement, (t), the first-order Taylor series expansion serves as a good approximation for the translated signal at time t+1. When boosting the temporal signal by and adding it back to I(x; t), we approximate that wave translated by (1+α)δ. For quickly changing image functions (i.e., high spatial frequencies), f(x), the first-order Taylor series approximations becomes inaccurate for large values of the perturbation, 1+αδ(t), which increases both with larger magnification and motion δ(t).

As a function of spatial frequency, ω, we can derive a guide for how large the motion amplification factor, α, can be, given the observed motion δ(t). For the processed signal, Ĩ(x, t) to be approximately equal to the true magnification motion, Î(x,t), we seek the conditions under which:

$$\tilde{I}(x,t) \approx \hat{I}(x,t)$$
$$\Rightarrow f(x) + (1+\alpha)\delta(t)\frac{\partial f(x)}{\partial x} \approx f(x + (1+\alpha)\delta(t))$$

Further rearrangement via the addition law of cosines and use of the following approximation:

$$\cos(\beta\omega\delta(t)) \approx 1$$

$$\sin(\beta\omega\delta(t)) \approx \beta\delta(t)\omega$$

leads to the following guideline:

$$(1+\alpha)\delta(t) < \frac{\lambda}{8}.$$

This guideline provides the largest motion amplification factor, α, compatible with accurate motion magnification of a given video motion δ(t) and image structure spatial wavelength, λ. In some videos, violating the approximation limit can be perceptually preferred and we leave the λ cutoff as a user-modifiable parameter in the multiscale processing.

In some embodiments, to process an input video by Eulerian video magnification, there are four steps a user needs to take: (1) select a temporal bandpass filter; (2) select an amplification factor, a; (3) select a spatial frequency cutoff (specified by spatial wavelength, λc) beyond which an attenuated version of a is used; and (4) select the form of the attenuation for α, either force a to zero for all λ<λc, or linearly scale a down to zero. The frequency band of interest can be chosen automatically in some cases, but it is often important for users to be able to control the frequency band corresponding to their application. In our real-time application, the amplification factor and cut-off frequencies are all customizable by the user.

One of skill in the art will understand that use of the term "color" as used herein this section and throughout the specification, may not only represent the optical spectrum. The word "color" may at times be used colloquially to identify a spectral frequency range (which may or may not be in the visible range). One of skill in the art will further understand that in embodiments, the techniques described herein may also function without the use of EVM, for example by detecting a change in green/red. However, such systems without EVM may have a significant reduction in sensitivity.

Of particular interest for the evaluation of intact tissue sites or in wounds, in some embodiments, Eulerian Video Magnification may be used to amplify subtle changes in pixel values relating to color using video collected from a CCD camera or RGB color detector. In some embodiments, a camera or RGB color detector may be combined with one or more standard LEDs to light the wound for visualization. For example, within an intact patch of skin or a wound bed, color changes may be indicative of favorable blood flow. For example, a value in the red spectrum via color detection may indicate blood flow, therefore, if the difference between the peak value and trough value of the color is small then it suggests that there is not much blood flow. Conversely, if the difference between the peak value and the trough value is relatively high, then this may indicate good blood flow to the tissue area.

Further, if the value is less red than there is likely to be insufficient oxygen. In some embodiments, color could also be used to generate an indication of blood oxygen (or with the light source modified to sense SP02 directly), to minimize the likelihood of damage to the capillaries upon treatment and to act as an alert if exsanguination does occur, potentially mitigating against potential harm that may be caused by application of NPWT. In some embodiments, EVM may be used on skin near a wound to monitor the motion of the adjacent skin due therefore identify whether the blood pulse is making it to the area of concern. Advantageously, absolute values need not be monitored to identify potential issues within the wound or tissue, instead monitoring of the difference in values is sufficient.

Pressure Injury Monitoring and Treatment

Pressure injuries (also known as pressure ulcers or bedsores) are injuries to soft tissues such as the skin and/or underlying tissue that occur due to obstructed blood flow caused by pressure. Pressure injuries are common on patients with limited mobility such as the elderly or the handicapped. Particularly susceptible to pressure ulcers are patients who are confined to a particular location such as a bed or wheelchair. Of particular interest in the field of medicine is the identification of pressure ulcers early on, before they become a serious injury. However, it can often be difficult to identify an area where a potential pressure injury will form due to early stage damage to the underlying tissue. Such damage may not be detectible by the naked eye by a clinician, but may be detectable by a monitoring system supported by EVM.

Figure 4:
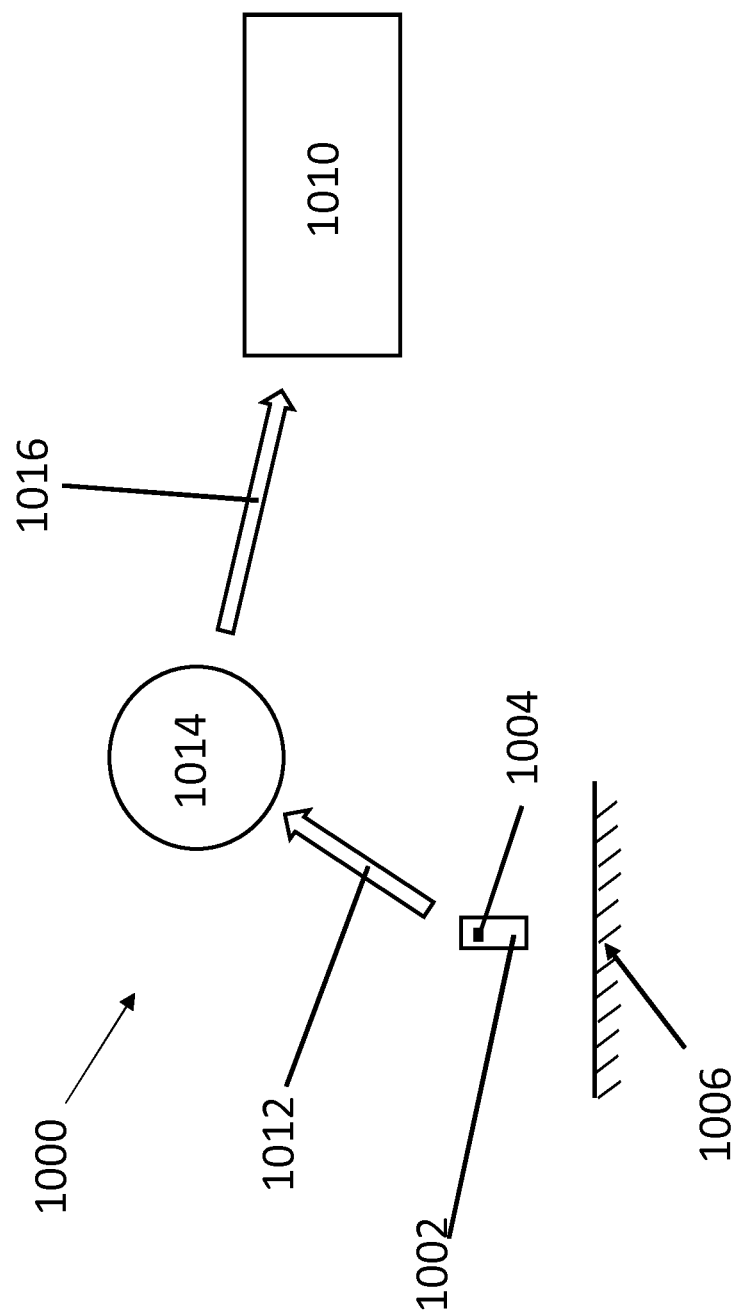
FIG. 4 illustrates an embodiment of a wound monitoring and treatment system.

FIG. 4 illustrates an embodiment of a system for pressure ulcer detection. However, one of skill in the art will understand that such a system may also be easily applied to other potential injuries or skin conditions. Further, the systems described here in relation to FIG. 4 are not limited to intact tissue, such systems may also be applied to an open wound.

FIG. 4 depicts an embodiment of a monitoring and treatment system 1000 incorporating EVM. Sensor construct 1002, may be positioned over a tissue sit of interest. In some embodiments, the sensor construct 1002 may comprise: one sensor, two sensors, three sensors, four sensors, five sensors, at least about 10 sensors, at least about 20 sensors, or more than 20 sensors. The sensor construct can be positioned above the tissue site, at an angle to the tissue site, under the tissue site, below the patient, or in any suitable position. In some embodiments, the sensor construct may collect video of a specific tissue site or the entirety of the patient.

One of skill in the art will understand that the sensor construct is not limited to a specific form or shape. For example, the sensor construct may be in the form of a mounted camera, a freely held camera, or a smart phone. The sensor construct may be part of a dressing or part of hospital bed or wheelchair. In some embodiments, a sensor construct may be in the form of a bundle of optical fibers that are contained within a blanket, bed system, sheet, and/or clothing. Such a form may allow for better visualization of a limited mobility patient confined to a bed. In some embodiments, the sensor could be positioned above a blanket or clothing and utilize visualization techniques that are not as limited by opaque objects, such as IR. Such a non-limited sensor construct may even be placed below a hospital bed or chair, providing visualization of the patient through the underside of the bed. The sensor construct may be in the form of a pressure matte, providing detailed information in close contact with the patient.

In some embodiments, the sensor(s) may collect information such as: pH, temperature, light, conductivity, impedance, capacitance, or other characteristics of the wound. In some embodiments, the sensors can provide information about the blood flow, moistness or dryness of the wound, lactate levels, or other characteristics of the wound. In some embodiments, all manner of sensor(s) may be incorporated in the system and they may be configured to measure parameters such as temperature, pH, oxygen, carbon dioxide, millimeter wave frequencies, conductivity, inductance, lactate, metallomatrix proteases, growth factors, optical absorption and reflectance including at infrared and UV frequencies and fluorescence, infection (level of bacterial burden and types of bacteria), or other characteristics of the tissue/wound environment. In certain embodiments, ultrasonic sensors with or without transducers may be used.

In some embodiments, thermistors or thermocouples may be used in place of the RGB sensor/CCD and light source described above. A grid or matrix of such sensors could be mounted and close-coupled to the tissue. These could be used in concert with other sensors (e.g. optical or EEG/ECG) to allow separation of the heart rate from the temperature noise of the environment (i.e. identifying the temperature changes that occur at the frequency of the heart pulse).

In some embodiments, coils for the generation of magnetic fields and/or RF signal may be placed within a dressing or in close proximity to the patient in place of or in addition to the CCD/RGB sensor. Coils may be mounted co-axially either nested or offset within the dressing. In some embodiments, a separate probe may be used to contain the coils, such a probe may be held against the tissue and transmit signals by wired or wireless connection. In certain embodiments, one or more accelerometers may be used for additional data input. Wobble switches and/or gyroscopes may also be used.

As described above, optical sensors may be used to measure wound appearance using an RGB sensor with an illumination source. In certain embodiments, another suitable optical sensor may be used. Both the RGB sensor and the illumination source may be pressed up against the skin, such that light would penetrate into the tissue and take on the spectral features of the tissue itself. Light propagation in tissue is dominated by two major phenomena, scattering and attenuation. For attenuation, as light passes through tissue, the intensity is lost due to absorption by various components of the tissue. Blue light tends to be attenuated heavily, whilst light at the red end of the spectrum tends to be attenuated least.

Scattering processes are more complex, and have various regimes which must be considered. The first aspect of scattering is based on the size of the scattering center compared with the wavelength of incident light. If the scattering center is much smaller than the wavelength of light, then Rayleigh scattering can be assumed. If the scattering center is on the order of the wavelength of light, then a more detailed Mie scattering formulation must be considered. Another factor involved in scattering light is the distance between input and output of the scattering media. If the mean free path of the light (the distance between scattering events) is much larger than the distance travelled, then ballistic photon transport is assumed. In the case of tissue, scatting events are approximately 100 microns apart—so a 1 mm path distance would effectively randomize the photon direction and the system would enter a diffusive regime.

Ultra-bright light emitting diodes (LEDs), an RGB sensor, and polyester optical filters can be used as components of the optical sensors to measure tissue color differentiation. Infrared and/or NIR of FIR may also be used. For example, because surface color can be measured from reflected light, a color can be measured from light which has passed through the tissue first for a given geometry. This can include color sensing from diffuse scattered light, from an LED in contact with the skin. In some embodiments, an LED can be used with an RGB sensor nearby to detect the light which has diffused through the tissue. The optical sensors can image with diffuse internal light or surface reflected light. Optical sensors can also be used to measure autoflouresence. Autoflouresence is used because the tissue is absorbing light at one wavelength, and emitting at another. Additionally, dead tissue may not auto-fluoresce and so this could be a very strong indication as to if the tissue is healthy or not. Due to blue light (or even UV light) having such a short penetration depth, it may be very useful for example to have a UV light with a red sensitive photodiode nearby (or some other wavelength shifted band) to act as a binary test for healthy tissue, which would auto-fluoresce at a very particular wavelength. In certain embodiments, an RGBW sensor may be used, but utilizing the white channel as the baseline to normalize the relative values of the RG and B.

Returning to the embodiment of FIG. 4, sensor construct 1002 with sensor 1004 may be positioned over a tissue site 1006. The sensor 1004 may be in communication 1012 with a controller 1014, via any suitable wired or wireless means. In certain embodiments, the sensor construct, sensor, and controller may all be one integrated apparatus, such as a smartphone, tablet, or other suitable computing device such as disclosed herein this section or elsewhere in the specification. In some embodiments, the sensor construct and the controller may be physically separated.

The communication from the sensor to the controller may be one-way, with the controller only receiving information from the sensor. However, alternatively, the communication 1012 between the sensor and the controller may be two-way with the sensor sending information to the controller but also receiving instructions and/or information from the controller. Controller 1014 may then be in communication, via wired or wireless means, with an output or alerting element 1010. Alerting element 1010 may be any suitable device configured to provide an alert. For example, the alert may be one or more of audible, haptic, or visual. The alert indicates to a caregiver that a pressure injury will form or may have already formed. Such an alert allows the caregiver to take pre-emptive action to avoid a pressure injury, such as to engage in pressure offloading of the patient such as by turning, adding stress relievers, performing treatments, or other suitable means.

In some embodiments, the alerting element may be part of a single integrated device with the sensor construct, sensor, controller, and alerting element. For example, such a device may be a smart phone, tablet, or other suitable computing device such as disclosed herein this section or elsewhere in the specification. In particular embodiments, the alerting element is physically separate from the sensor and controller. However, various embodiments the alerting element may be integrated with the sensor construct but not the controller, or the alerting element may be integrated with the controller but not the sensor construct.

The controller may be any processing device capable of executing software, such as disclosed herein this section or elsewhere in the specification. For example, the processing device may be a processor, PC, tablet, smartphone, or other computer capable of running host software.

When the system 1000 is operating, the sensor 1004 collects video data from the tissue site 1006 over time. This video data may be collected and stored to be transmitted to the controller 1014 at periodic intervals and/or the video data may be continuously transmitted to the controller. The tissue site video data collected by the sensor 1004 may be of any data potentially collected from any sensor disclosed herein this section or elsewhere in the specification, but suitably visible optical data or IR data. In some embodiments, the sensor may collect video of the tissue site indicative of tissue that may have poor blood flow. As will be described in greater detail below, in such instances the alerting element is configured to deliver an alert to direct a caregiver to the possibility of formation of a pressure injury. In some embodiments, the sensor 1004 may detect the edge of a wound 1006 and then collect video of the edge of the wound, for example collecting optical data including motion and color information. As described previously, EVM can be used to detect very subtle changes in individual locations/pixels within a video. In certain embodiments, EVM may be applied to a single pixel. Such a single pixel may be from a single sensor or combined/averaged from multiple sensors. In some embodiments, multiple pixels may be drawn from a single sensor or form multiple sensors such as in an array. For motion detection (i.e. identification of tissue movement due to blood pulsing within it as described elsewhere), multiple, closely aligned pixels may be required. However, in some embodiments, single pixels or multiple pixels from a single sensor may be used.

Video data collected by the sensor may then be transmitted to the controller 1014, whereby the controller applies EVM to the video. As described previously, EVM, can be used to detect very subtle changes in individual locations/pixels within a video. Changes in color and/or motion may be indicative of blood flow to the tissue, poor blood flow may indicate the potential for a pressure injury. Further, less red tissue may indicate the existence of pressure limiting blood flow to particular tissue site.

As will be described in greater detail below, change in color, motion, or another parameter may indicate that an alert should be generated by the alerting element. If an alert is merited, the controller may communicate 1016 with the alerting element 1010 and direct the alerting element 1010 to generate an alert. Such communication may be in the form of a feed-back loop, allowing for the alerting element to continue to provide alerts until the tissue site is no longer at risk for a pressure injury. In some embodiments, the alert can become progressively more insistent, via increase in sound, light, or other suitable means, if no action is taken. The alert may vary in intensity, depending upon the risk of formation of a pressure injury and/or the severity of the pressure injury.

In some embodiments, time series analysis algorithms such Auto Regressive Integrated Moving Average (ARIMA), Generalized Autoregressive Conditional Heteroskedasticity (GARCH), or Cusum (or cumulative sum) can be used to determine changes in values between pixelslocations in video frames over time, such as described herein this section or elsewhere in the specification. For example, indicative of blood flow or motion. Cusum can be defined as the running sum of the difference between each sample and the mean (e.g., in the absence of change, Cusum is zero). Cusum can be used to track variations in the underlying variable, including one or more of redness, delta-red, motion, or a calculated treatment parameter. Determined Cusum value or values can be compared to one or more thresholds to determine blood flow and/or motion and/or any suitable value disclosed herein this section or elsewhere in the specification.

In some embodiments, EVM may be used detect very slight movements or motion of the skin and underlying tissue such as tremors or vibration of the skin and underlying tissue. Such tremors or vibration of the skin may be used for diagnosis, such as via any method described herein this section or elsewhere in the specification. In some embodiments, vibration or tremors may be used to diagnose neurological diseases such as multiple sclerosis or Parkinson's disease. Further, identification of tremors or vibration may be utilized to detect muscle strain. For example, a video image may be collected of a tissue site via any suitable method disclosed herein, followed by amplification via EVM. Such amplified video may then be analyzed to determine an amount of vibration/tremors, which can then compared to a threshold associated with Parkinson's disease or another similar disease. If the vibration/tremor of the tissue exceeds a threshold, then an alert may be generated such as any alert disclosed herein this section or elsewhere in the specification.

In certain embodiments, a proportional integral derivative algorithm (PID) style loop may be used by the NPWT pump, to ensure that the integrated blood flow is suitable to maintain the tissue in an acceptable condition and optimal pressure may be used to ensure optimal blood flow without producing excessive blood flow. PID style loops are well-known in the art for adjusting the output of a pump as a process variable changes. In certain embodiments, the response to the treatment parameter measurements may be self-optimizing such the software may explore optimum responses, per a change in treatment parameter by examining the treatment/response curve. For example, if a particular change in a variable results in a dramatic shift in treatment parameter, the system may adjust to only change the output for a desired amount. For example, a variable may be adjusted until a maximum difference in the EVM output is achieved. In certain embodiments, it may be advantageous to build in a delay between therapy adjustments to allow time for the body to respond to the previous change in therapy.

The acceptable red-delta value could be modified slightly (by the clinician) to allow for pain-susceptible patients where beneficial but sub-optimal therapy is preferable to pain. A continuous high-red value (with minimal red-delta) would also be an indicator of bleeding, one of the highest risks of NPWT. Such a control system, may also be suitable for pain management and bleeding-identification systems integrated into software packages, such as software systems associated with NPWT pump systems. For example, while a specific location of bleeding may be detected as pulsatile, once blood flows away from the breach it will no longer have a pulse so the color maybe identified as red and not vary at the pulse rate Thus, such an indicator can be identified as bleeding and flagged as a cause for immediate intervention, therefore trigger the shut-down of NPWT to minimize exsanguination before the intervention is achieved.

Advantageously, the use of EVM allows the system to be responsive to changes at the tissue site, rather than simply being responsive to clinician observations. Such a system identifies the true blood flow within the specific patient. Current "standard" protocols require turning of a patient after a specific time (a shorter time for higher risk patients). The use of the system of FIG. 4 does not require any subjective assessments of the risk to the patient, instead the system directly identifies whether blood is being restricted from the tissue therefore minimising unnecessary intervention while ensuring that all required intervention is performed.

Such a reactive system may also be pro-active in avoiding ischemia, as low blood flow could be detected early and treated before traditional detection. Further, the system 1000 may allow for treatment of oedema by providing an alert upon the identification of areas of oedema, thereby minimizing oedema by increasing effective compression.

Figure 5A:
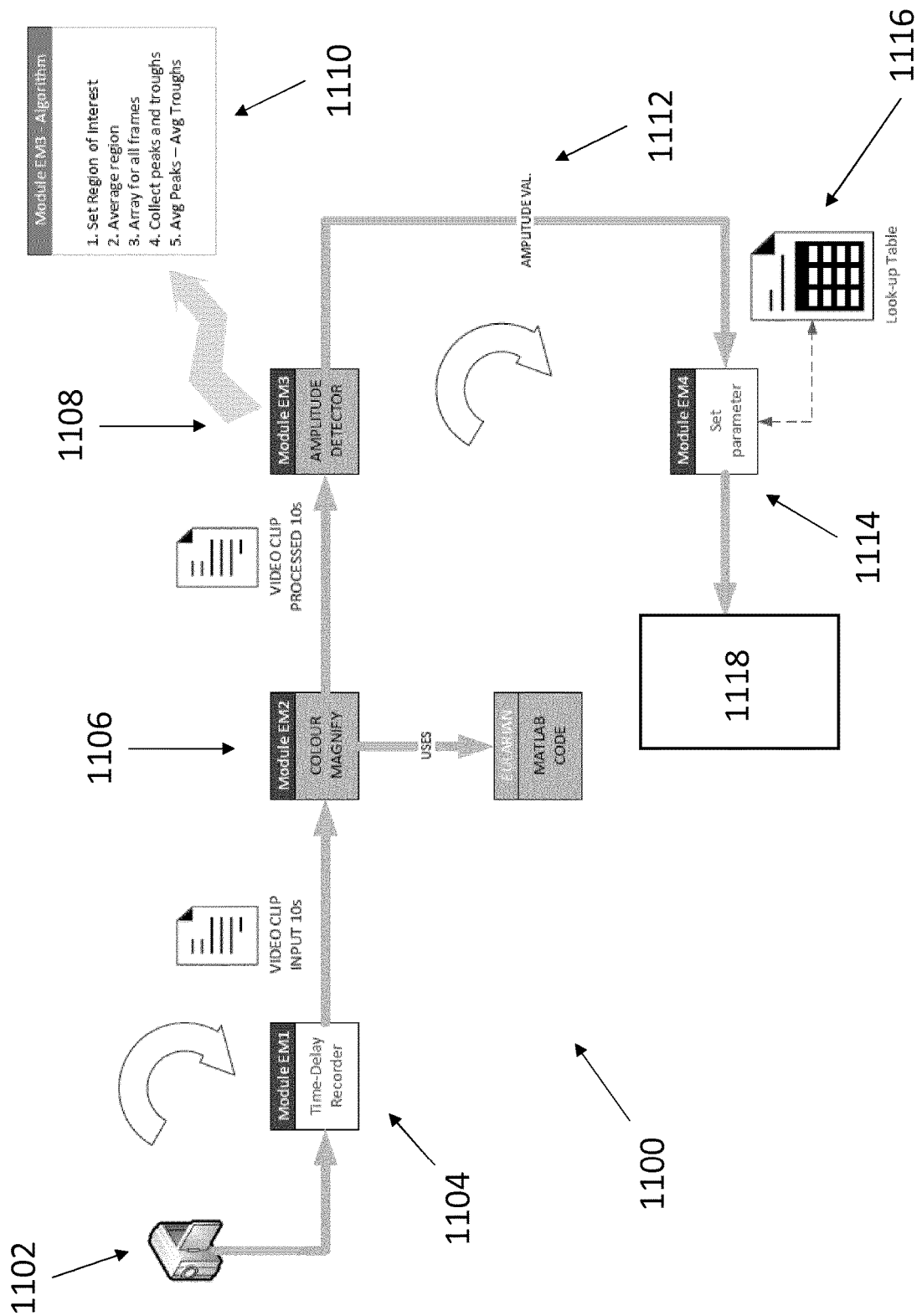
FIG. 5A illustrates embodiment of a wound monitoring and treatment system.

FIG. 5A depicts an embodiment of a method of EVM processing in combination with an alerting element 1100, providing greater detail on the steps taken from collection of video data to the alert shown above in FIG. 4. Although FIG. 5A makes reference to "modules," one of skill in the art will understand that such modules may be software steps that may be completed on one or more computing devices, such as the controller described above in relation to FIG. 4. Such computing devices may be any computing device disclosed herein this section or elsewhere in the specification, for example a controller, smartphone, server, or general computer such as a laptop or desktop. In the first step, a video capture device 1102, such as a camera or other sensor device, such as disclosed herein this section or elsewhere in the specification, collects video of a tissue site of interest. Video may be taken in any suitable manner or suitable location such as described herein this section or elsewhere in the specification.

Next, a video clip of a desired length 1104, for example 10 seconds, is collected and stored 1104. It will be understood by one of skill in the art that the video clip may be of any suitable length, for example, about: 1 second, 5 seconds, 10 seconds, 15 seconds, 30 seconds, 60 seconds, 5 minutes, 1 hours, 12 hours, 24 hours, or more than 24 hours. Further, in certain embodiments, the video is continuously transmitted and continuously processed for analysis. The embodiment disclosed in FIG. 5A may be performed with clips of video or with continuously transmitted video. In some embodiments, the video may contain at least about: 5 frames per second, 10 frames per second, 20 frames per second, 30 frames per second, 45 frames per second, 60 frames per second, 75 frames per second, 90 frames per second, 120 frames per second, or more than 120 frames per second.

Once the video has been captured, the values of each location/pixel within the video may be magnified via EVM 1106. Such an EVM algorithm may be executed within any suitable software medium, for example MATLAB code. In some embodiments involving a video taken with a standard camera in the visible light spectrum, the EVM algorithm may serve to amplify the color values of the image. For example, the EVM algorithm may amplify the red color values within the video. As described above, redness may be an indicator of blood perfusion to a particular tissue.

Once the video clip or continuously streamed video has been processed, a "treatment parameter" is determined. For example, if a change in redness is of interest, the change in redness or delta-red may be determined for every location and/or pixel of interest and used in the calculation of the treatment parameter 1108. In some embodiments, the treatment parameter may be calculated by the following steps 1110. First, a region or regions of interest are set within a video frame, by selecting one or more pixels within a particular area of the video frame.

Next, the pixels within the region are averaged to provide an average value per region per frame. The averaging process may incorporate sophistication to eliminate outliers that may be introduced in to the system. Then, an array is generated for the average values over time as additional data is collected with each consecutive frame of the video. From these consecutive frames, the highest values and lowest values may be collected, for example the highest and lowest red values. Then, the average peak value may be calculated for the highest values and the average trough value may be calculated from the lowest values. Subtracting this highest average peak value from the lowest average trough value then gives a single value. This value can then be calibrated 1112 to equate to a single parameter number, referred to as the "treatment parameter." As will be described below, the "treatment parameter" can be compared to a value in a lookup table 1116 to indicate whether a NPWT device should increase or decrease application of negative pressure 1118. If the treatment parameter is determined from changes in red color within a video, then higher treatment parameters would tend to indicate good blood perfusion, while lower treatment parameters would tend to indicate poor blood flow.

Figure 5B:
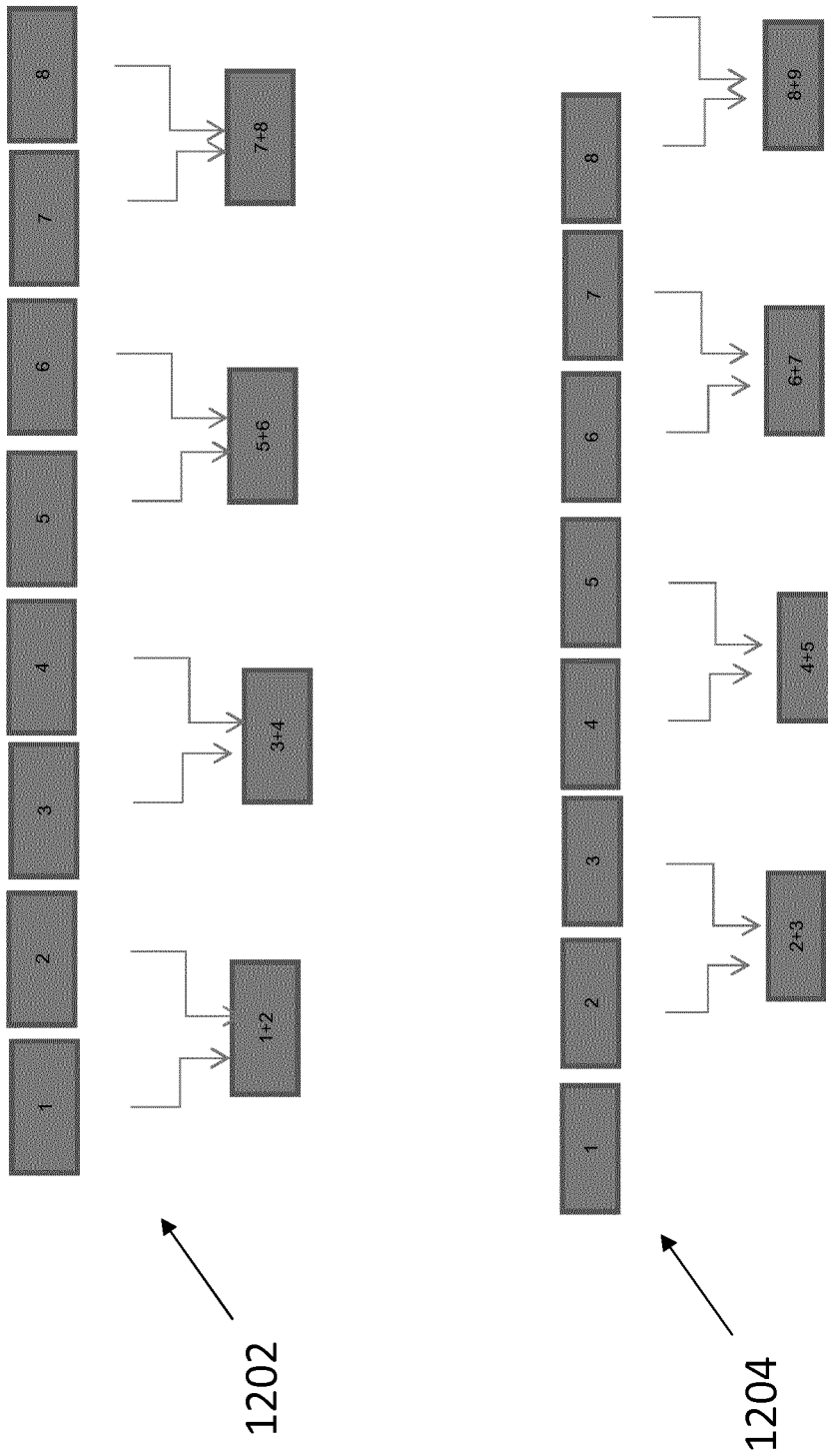
FIG. 5B illustrates an embodiment of a sampling method for sampling frames from a video.

As depicted in FIG. 5B, which can be implemented by a controller, in certain embodiments, to reduce the use of a high-rate sampling, multiple frames could be combined to provide a signal at a lower frame rate. For example, the values from frame 1 and frame 2 may be combined, along with the values from frame 3 and frame 4, and so on 1202. Then the combination of 1+2 may be compared with the value of 3+4 to identify both the highest and lowest signals for us in calculation of the treatment parameter. In some embodiments, the combined values could be calculated in a different manner 1204, for example, by combining frames 2 and 3, to be compared to a combination of frames 4 and 5, etc. Once the values within each frame are combined, then the amplitude of the change in values may be calculated, in a similar fashion as described above by subtraction the average trough value from the average peak value. The treatment parameter may be calculated from changes in red value in a video that has undergone EVM. However, in further embodiments, any particular color value may be used such as blue or green. Further, any particular value may be used that can be derived from video generated by any of the sensors disclosed herein this section or elsewhere in the specification, such as spO2 or infrared.

In certain embodiments, a possible analysis step may be to integrate blood flow values over time, potentially identifying whether the cumulative restriction of blood flow indicates a risk of pressure injury. Such an indicated risk may trigger an alarm such as described herein this section or elsewhere in the specification.

Returning to FIG. 5A, once the treatment parameter has been calculated, the controller may compare the treatment parameter 1114 to a pre-set desired value or range. Such a desired value or range may be pre-set by the controller or by a clinician. Such a desired value or range may be determined from literature, via experimentation, via algorithm, or via other suitable means. Regardless, the use of a desired value or range allows the controller to compare the calculated treatment parameter to the desired value or range in order to direct the alerting element to produce an alert. If the treatment parameter remains at a desired value or range then no alert may be generated, or an indicator may be generated that indicates healthy tissue.

In certain embodiments, the response to the treatment parameter measurements may be self-optimizing such the software may explore optimum responses, per a change in treatment parameter by examining the treatment/response curve. For example, if a particular change in a variable results in a dramatic shift in treatment parameter, the system may adjust to only change the variable for a desired amount. For example, a variable may be adjusted until a maximum difference in the EVM output is achieved. In certain embodiments, it may be advantageous to build in a delay between therapy adjustments to allow time for the body to respond to the previous change in therapy.

Diagnosis and Treatment

One of skill in the art will understand that the system described above in relation to FIGS. 4-5B may also be applicable to a wide range of tissue phenomena and a wide range of treatment responses. For example, in certain embodiments, instead of providing an alert upon detection of poor blood flow, the controller may be configured to communicate with a NPWT device, such as described above in relation to FIGS. 1-2C. Such a system may provide NPWT to a wound site when the controller indicates that treatment is merited.

One of skill in the art will further understand that the embodiments involving EVM described above in relation to FIGS. 4-5B lend themselves well to diagnosing the condition of intact tissue or the condition of a wound. FIG. 6 illustrates an embodiment of a method 1300 for evaluating a wound using EVM in combination with evaluation algorithms. The method 1300 can be performed by a sensor and a controller. In 1302, video is collected from a tissue site via any of the means described herein this section or elsewhere in the specification, and using any sensor described herein this section or elsewhere in the specification. Such a sensor may be positioned on a smartphone. However, in certain embodiments, the smartphone may be a tablet or other suitable computing device such as disclosed herein this section or elsewhere in the specification. Nevertheless, for the purposes of explaining the embodiment of the method of FIG. 6, the term "smartphone" will be used.

The video 1302 may be collected of any tissue site of interest, for example a tissue site suspected of possible injury undetectable by the naked eye or a tissue site that is being considered for possible treatments such as NPWT. Once the video has been collected or as it is collected in real-time, EVM may be applied to the video according to the methods described herein this section or elsewhere in the specification 1304. Once EVM has been applied, a processor or controller contained within the smartphone may analyse 1306 the image to calculate delta values (change values) for certain pixels and/or regions, similar to the methods described above in relation to FIGS. 5A-5B. Once the delta values have been calculated, the processor may overlay the delta values on top of the video or a static image to display an overlain image to a caregiver. Such an overlay may be displayed by any suitable, such as disclosed herein this section or elsewhere in the specification, for example, a smartphone screen. In certain embodiments, an algorithm may be used to cross-reference particular features with a database of tissue types and phenomena. Therefore, the overlay may include information such as identifying a blood vessel, a wound, a subcutaneous injury, a hematoma, an oedema, or any other suitable tissue or phenomena.

In further examples, for deep tissue injury diagnoses, a clinician and/or the algorithm may identify a region of tissue for application of offloading. Further treatments to the identified tissue may be to apply a dressing such as Allevyn Life by Smith & Nephew. Further treatments could include a recommendation for application of massage and/or skin-care products to the site. In certain embodiments, NPWT may be merited to an unbroken tissue site, such as disclosed earlier in the specification; for example, a Pico device by Smith & Nephew may be applied.

The overlay 1306 may provide treatment information 1308 to the clinician. For example, if the delta value(s) in a particular area of the wound or tissue site are/is low, as described above in relation to FIGS. 4-5B, this may indicate poor blood flow to a particular area. Such an analysis may indicate to the physician that a treatment 1310, such as NPWT is merited to treat such tissue. In some embodiments, the smartphone may be configured to directly communicate with a NPWT device to start treatment, either automatically or via manual prompt. Alternatively, if the delta is low but the overall color value is higher, this may indicate the presence of a contusion. Alternative meaning for a low delta could be the presence of oedema. In certain embodiments, for oedema NPWT and/or compressing may be recommended. In the case of possible ulcers, such as a diabetic ulcer, then off-loading by removing pressure may be recommended.

For identification of necrotic tissue, such tissue may be treated through the use of waterjet debridement (e.g. Versajet by Smith & Nephew), plasma debriders, and/or enzymatic debriders, such as collagenase. Necrotic tissue may also be debrided using more traditional techniques such as mechanical cutting or abrading devices. In the scenarios of monitoring venous leg ulcers, for example, an area where minimal change in blood or very low oxygenated blood is identified, this may show a blocked vein and/or a perforated vein. In such cases surgical intervention for removal of the vein or blockage may be recommended. Advantageously, such a diagnosis may improve upon current methods using ultrasound (from behind the wound, to avoid contamination).

One of skill in the art will understand that all of the treatment methods described herein this section or elsewhere in the specification, may be autonomous such that a treatment device may communicate with the computing device and be instructed directly to apply treatment without human intervention. Such treatment could combine multiple therapies, such as NPWT and debridement, as merited by the analysis of the tissue via EVM or other suitable means.

In certain embodiments, further information may be collected around the edges of a wound. For example, the smartphone may identify the edge of the wound by identifying that skin colour in that particular location is changing by less than the wound area during a pulse or physical movement reduced on healed skin. Such an approach may work in concert with a semi-static colour measurement to augment the identification of skin vs. wound colouration. In some embodiments, the data may be transmitted from the dressing either to the wearer's phone, to a nurses communication-enabled device, to a data hub, to an indication station, or to any suitable system or device. A negative trajectory may be highlighted to perform an intervention and upgrade the treatment path. A positive healing pathway may identify that the current treatment is successful and can be continued or even downgraded to a cheaper and/or less aggressive treatment.

Returning to potential analysis of a tissue site, as described elsewhere damaged tissue may not have much blood flow and may therefore have a low delta value. However, as the tissue heals, the area showing a tissue parameter/delta value of healthy tissue should increase. If the healthy area is increasing quickly then there may be no requirement to utilize further aggressive and expensive treatments as the body is healing on its own. If the area that is healthy is not increasing then a greater intervention may be required (e.g. the raise to a more expensive pathway, for example, changing from a passive dressing to NPWT or another therapy such as antimicrobials).

If certain tissue regions have a delta close to zero, than this may indicate that the tissue is necrotic. In such instances, the smartphone algorithm may recommend removal of such tissue via debridement, such as via plasma debrider, water debrider, or enzymatic debrider. In some embodiments, the smartphone could be configured to communicate directly with a plasma or water debrider and apply debridement to the wound site until the zero delta tissue is removed and only healthy tissue remains and is identified with a positive delta.

In certain embodiments, the smartphone sensor may be used to identify the presence of blood vessels that may not be apparent to the naked eye. Such detection may be valuable for guiding a clinician in the application of NPWT because application of NPWT directly to a blood vessel can be dangerous. Areas with blood vessels close to the surface will likely result in a high delta value due to the change in color or other parameter (such as motion) between blood pulses. However, to avoid false positives from very small capillaries, it may be necessary to modify the region selection such that a number of pixels are selected, otherwise a single pixel could show a very high delta value, but only due to a single capillary. In certain embodiments, the smartphone could contain algorithms to detect the present of exudate over the top of the wound, thereby guiding a physician toward the removal of such exudate.

Returning to FIG. 6, in certain embodiments, video collection 1302 could occur between wound dressing changes. Conventional dressings may be changed a few times a day, once a day, a few times a week, once a week, or less often than once a week. Once video of the wound between dressing applications is collected, EVM could be applied, providing enhanced information about the state of the wound between dressing changes. Comparison between video taken at different time points between dressing changes may provide a caregiver with enhanced information regarding the state of the wound, such as by analysing the image and applying an overlay 1306. The smartphone may be configured with an algorithm to provide a treatment recommendation to the clinician, depending on the changing characteristics of the healing wound, such as the amount of wound closure or the present of undesirable tissue types In some embodiments, for a size comparison of a wound between dressing changes, a fixed-size 2D barcode (or other fixed image) may be used to identify the size baseline (and orientation). In particular embodiments, a colour-based algorithm may be used to identify common features between the wound at different times in order to scale the image. A first image from an earlier treatment time may be ghosted over a new image to allow the caregiver to align and scale the wound images in time. In certain embodiments, multiple cameras may be used to identify the size and/or the camera rangefinder may be used to identify the size and re-scale.

Embodiments Using Additional Signal Inputs
Magnetic Induction Tomography

In some embodiments, the systems and methods described above in relation to FIGS. 4-6 may be used with different types of signals such as the signal provided from magnetic induction tomography (MIT). In some embodiments, with the multiple-coil options, one coil may be pulsed at a high repeat rate (for example in the range 5 to 25 'frames' per second) to capture "frames" to identify the underlying heart rate. The rest of the coils may then be used at a rate closer to that heart rate which may allow the "shutter speed" to be reduced (e.g. to closer to 2 to 5 'frames' per second) leading to a longer exposure without as much noise from the heart rate on the signal. In some embodiments, tissue damage such as pressure insult may then be identified through either or both of a "static" signal where little delta change is observed at the pulse frequency and/or in a Eulerian amplified signal with changes between amplified frames. In certain embodiments utilizing multiple coils, where each coil can interfere with the next, the difference between the coils at the heart frequency could be used to remove the noise due to the presence of the other coils. For example, bruising or other damage in the tissue may be identified as a location at which the heart-rate pulse does not change the tissue inductance between peak and lowest pulse pressure. This information may be used to supplement the "static" identification of whether there is blood (which could be healthy tissue, a bruise or a clot) or an absence of blood (ischemia), therefore allowing separation of the different states with blood present.

In certain embodiments, the output may be an EVM video identifying the change in inductance (with different colours representing different inductances), a numerical value, or a diagnosed value identifying the presence of a volume to which blood is not going (ischemia) or which is damaged (bruise/clot) and triggering an alert from a alerting element such as disclosed herein this section or elsewhere in the specification.

Ultrasound

In certain embodiments, and as described above in relation to the disclosed sensors, Eulerian Video Magnification may also be applied to ultrasound video of a tissue site 1302. In some embodiments, tissue damage such as pressure insult may then be identified through either or both of a "static" signal where little delta change is observed at the pulse frequency and/or in a Eulerian amplified signal with changes between amplified frames. As with magnetic induction tomography described above, bruising or other damage in the tissue may be identified as a location at which the heart-rate pulse does not change the tissue noise response between peak and lowest pulse pressure. This information may be used in addition to the "static" identification of whether there is blood (which could be healthy tissue, a bruise or a clot) or an absence of blood (ischemia), therefore allowing separation of the different states with blood present.

In certain embodiments, the output may be an EVM video identifying the change in inductance (with different colours representing different inductances), a numerical value, or a diagnosed value identifying the presence of a volume to which blood is not going (ischemia) or which is damaged (bruise/clot) and triggering an alert from a alerting element such as disclosed herein this section or elsewhere in the specification.

Temperature Signals

In certain embodiments, the systems and methods described above in relation to FIGS. 4-6 may be applied to temperature signals. As with magnetic induction tomography and ultrasound, bruising or other damage in the tissue may be identified as a location at which the heart-rate pulse does not change the tissue noise response between peak and lowest pulse pressure. This information may be used in addition to the "static" identification of whether there is blood (which could be healthy tissue, a bruise or a clot) or an absence of blood (ischemia), therefore allowing separation of the different states with blood present.

In certain embodiments, the output may be an EVM video identifying the change in inductance (with different colours representing different inductances), a numerical value, or a diagnosed value identifying the presence of a volume to which blood is not going (ischemia) or which is damaged (bruise/clot) and triggering an alert from a alerting element such as disclosed herein this section or elsewhere in the specification.

In some embodiments, thermistors or thermocouples could be used in place of the RGB sensor/CCD and light sources described above in relation to FIGS. 4-6. A grid or matrix of such sensors may be mounted close-coupled to the tissue. These sensors may then be used in concert with other sensors (e.g. optical or EEG/ECG) to allow separation of the heart rate from the temperature noise of the environment (i.e. identifying the temperature changes that occur at the frequency of the heart pulse). In certain embodiments, infrared measurements, such as disclosed herein this section or elsewhere the specification may be used for temperature measurements.

Electromagnetic Generator

In certain embodiments, one or more electromagnetic (EM) generators and receivers may be mounted in an object such as a bed or chair, pointing upwards, similar to the embodiments described above in relation to FIG. 4. In some embodiments, the materials of the mattress and bedding may be transparent to the EM frequency (e.g. millimetre wave). The source and sensor may also be remote with an EM guide such as an optical fibre directing the waves to the correct location and direction. In some embodiments, the emission location may be either beneath the mattress/padding or at some point closer to the occupant, but may be suitably padded to minimise point loading, risking pressure injury. In a bed implementation, the source may shine through the bed/bedding and be reflected off the tissue of the occupant of the bed. The EM wave may then be collected at the receiver and EVM performed on this returned wave. The output of the amplification, as processed by an algorithm indicating a need for intervention, may be sent to either a bed/chair-mount indicator with an alarm element such as disclosed herein this section or elsewhere in the specification or communicated to an external alarm element by a wired or wireless connection. If the patient is incontinent, urine and other waste will also reflect the millimetre wave signal and may be indicated as an event. Incontinence is a contributing factor to tissue breakdown through maceration, therefore identification and quick intervention may improve outcomes.

Langer's Lines

In some embodiments, the systems and methods described above in relation to FIGS. 4-6 may be used to identify and utilize Langer's lines as a surgical guide for forming incisional wounds. Langer's lines are topological lines drawn on a map of the human body corresponding to the natural orientation of collagen fibers in the dermis, generally parallel to the orientation of the underlying muscle fibers. Knowledge of the direction of Langer's lines within a specific area of the skin can be important for surgical operations, particularly cosmetic surgery. When possible, a surgeon will preferably cut in the direction of Langer's Lines within a given tissue site. Surgical incisions made parallel to Langer's lines tend to heal more quickly and produce less scarring compared to surgical incisions that cut across Langer's Lines. Incisions made perpendicular to Langer's lines have a tendency to pucker and remain obvious to the naked eye, although sometimes this is unavoidable depending on the required surgical intervention. For example, the orientation of stab wounds relative to Langer's lines can have a considerable impact upon the presentation of the wound. Further, keloids are more common for incisions across Langer's Lines. General maps of Langer's Lines are available to give a surgeon a general understanding of the position and orientation of Langer's Lines across the entire human body, however, such maps are not perfectly accurate and do not capture the particular Langer's Line orientations within every patient due to variation across populations and individuals. In some cases, use of a real-time image enhancement technology, such as the EVM embodiments described above in relation to FIGS. 4-6, may be advantageous to provide a surgeon with proper guidance regarding incision site.

Figure 7:
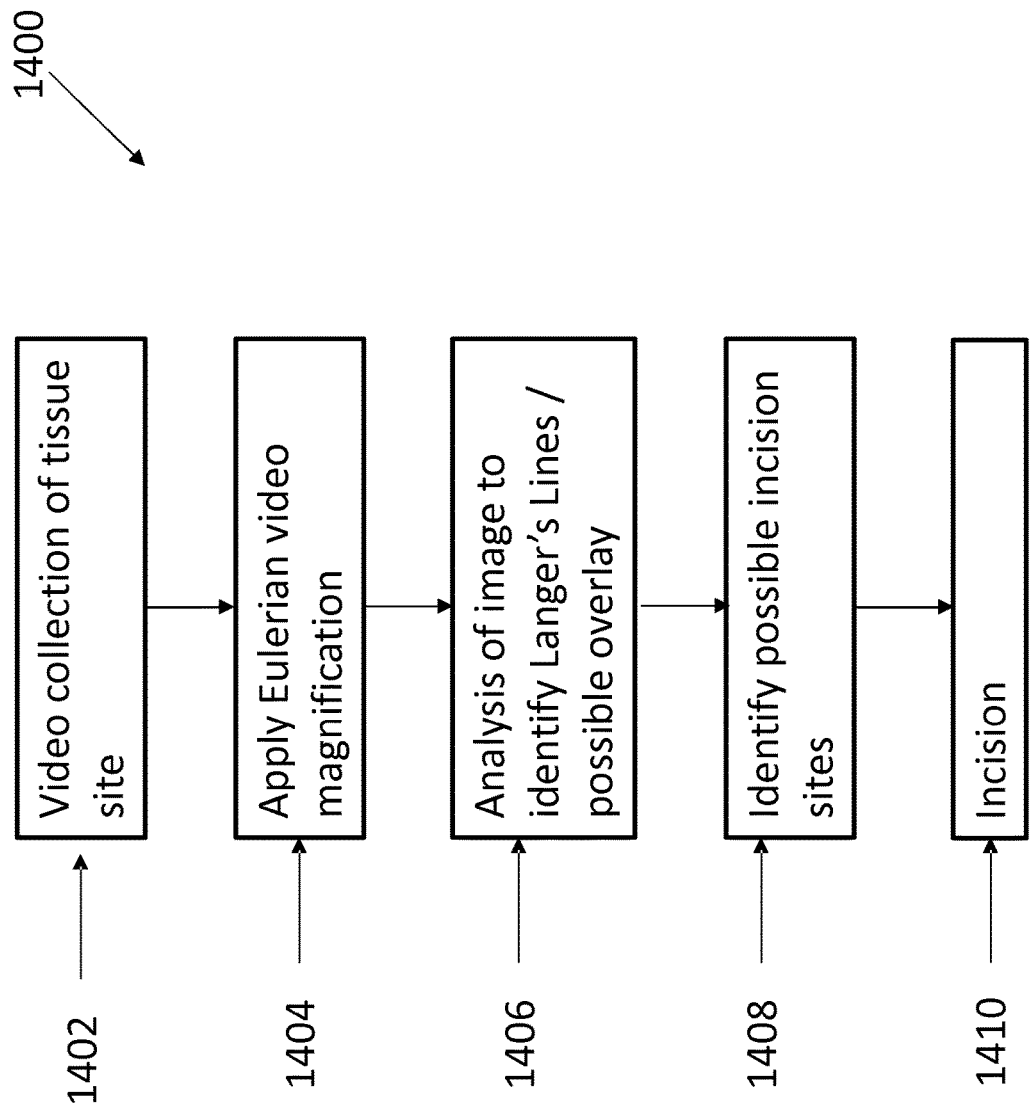
FIG. 7 illustrates an embodiment of a method and/or system for mapping Langer's Lines and identifying an incision site.

FIG. 7 illustrates an embodiment of a method and/or system 1400 for evaluating a potential incision site using EVM in combination with evaluation algorithms that identify Langer's Lines. The method and/or system 1400 can include and/or be implanted by a sensor and a controller. In 1402, video is collected from a tissue site via any of the means described herein this section or elsewhere in the specification, and using any sensor described herein this section or elsewhere in the specification. Such a sensor may be positioned on a smartphone. However, in certain embodiments, the smartphone may be a tablet or other suitable computing device such as disclosed herein this section or elsewhere in the specification. Nevertheless, for the purposes of explaining the embodiments of FIG. 7, the term "smartphone" will be used.

The video 1402 may be collected of any tissue site of interest, for example a tissue site suspected of possible injury undetectable by the naked eye or an obviously wounded tissue site. In some embodiments, the video may be collected of a tissue site identified as a potential surgical site, requiring access to an internal tissue site through surgical incision. As described above, Langer's Lines are used by surgeons to identify surgical incision sites.

Once the video has been collected or as it is collected in real-time, EVM may be applied to the video according to the methods described herein this section or elsewhere in the specification 1404. Once EVM has been applied, a processor or controller contained within the smartphone may analyse 1406 the video image to identify Langer's Lines within the tissue site by calculating delta values (change values) for certain pixels and/or regions, similar to the methods described above in relation to FIGS. 4-6. For example, the processor or controller may identify areas of skin tension based on amplified video data of static tissue or tissue undergoing movement. Areas of skin tension may be used to identify Langer's Lines. In some embodiments, Blaschko's Lines and/or Kraissl's lines may also be identified by amplifying video of static or moving skin. In certain embodiments, skin may be pinched or otherwise manipulated to create wrinkles in the skin, corresponding to Langer's Lines. In certain embodiments, EVM may amplify video of skin such that different tissues are identified, such as collagen bundles within the skin. The processor or controller may utilize these collagen bundles to map and identify Langer's Lines.

Once the delta values have been calculated, the processor may overlay the delta values on top of the video or a static image to display an overlain image to a caregiver. Such an overlay may be displayed by any suitable display, such as disclosed herein this section or elsewhere in the specification, for example, a smartphone screen. In certain embodiments, an algorithm may be used to cross-reference particular features with a database of tissue types and phenomena. Similar to the above embodiments as disclosed in relation to FIGS. 4-6, the overlay may include information such as identifying a blood vessel, a wound, a subcutaneous injury, a hematoma, an oedema, or any other suitable tissue or phenomena. Alternatively or in combination with the above, the processor may overlay Langer's Lines based on database information regarding the most common positions and orientations of Langer's Lines in the human body.

In certain embodiments, the overlay may include Langer's Lines applied over the image or video of the tissue site in a topographical map. Such an overlay may include solid lines to indicate the positions of the Langer's Lines and/or arrows to identify the direction and orientation of the Langer's Lines. The Langer's Lines may then be utilized by a surgeon to identify the proper orientation and location of a potential incision site 1408. Once an incision site has been identified, the surgeon may make an incision 1410 while video continues to be collected and amplified. Therefore, the surgeon may monitor minute changes in the tissue site, during surgery.

In some embodiments, an alert may be generated when a particular threshold and/or parameter relating to Langer's Lines is reached. For example, a controller, such as any controller disclosed herein this section or elsewhere in the specification, may provide an alert to the caregiver to notify the surgeon that a particular incision is not aligned with the Langer's Lines. Such an alert may be provided via any means disclosed herein this section or elsewhere in the specification. Further alerts may be provided when other thresholds and/or parameters are reached, such as any of the thresholds and/or parameters disclosed herein this section or elsewhere in the specification.

Magnetic Induction Tomography with Ultrasound

As described above, ultrasound may be used to image a tissue site. However, ultrasound may also be used therapeutically to accelerate healing. In some embodiments, therapeutic ultrasound may be applied at a frequency of between about: 0.5-10 MHz, such as about 1-5.0 MHz, or about 1 to 3.0 MHz. Such healing therapy may be performed on internal tissue sites, such as a ligament in the shoulder, knee, or other suitable location. However, although therapeutic ultrasound may be delivered to an internal tissue site, the progress of said healing of the internal tissue site is typically difficult to monitor. For example, conventional imaging means may not be able to detect minute changes in the tissue, thereby making it difficult to determine whether accelerated healing is occurring. Further, conventional imaging means may not be able to monitor delivery of the ultrasound in real-time, thereby making it difficult for a clinician to understand the efficacy of the ultrasound treatment.

Figure 8:
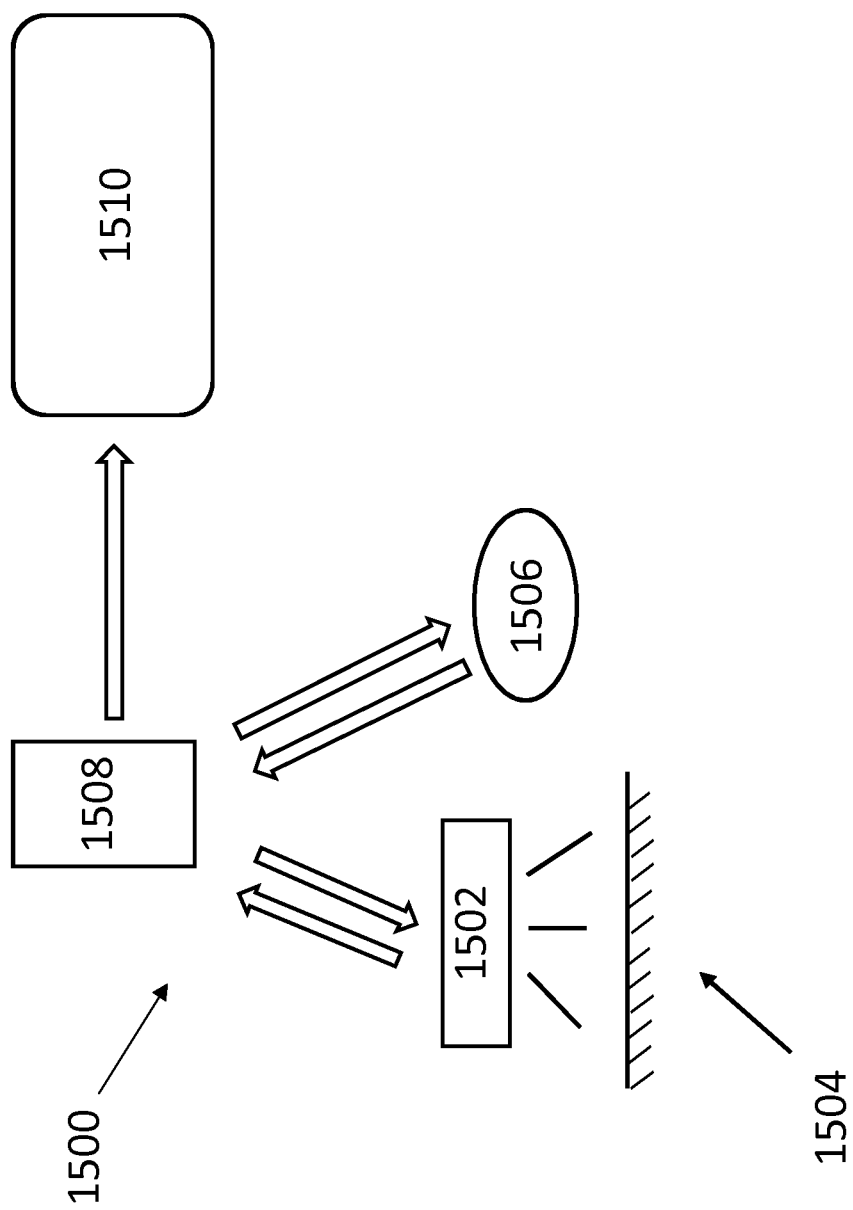
FIG. 8 illustrates an embodiment of a system for monitoring the treatment of a tissue site with ultrasound via magnetic induction tomography.

FIG. 8 illustrates an embodiment of a treatment system 1500 that utilizes therapeutic ultrasound delivery from an ultrasound device 1502 to an internal tissue site 1504 in combination with monitoring via magnetic induction tomography (MIT) 1506, described above. One of skill in the art will understand that such a tissue site may encompass any suitable tissue site, such as the ligaments of the shoulder, knee, elbow, or other suitable joint. One of skill in the art will further understand that the methods and devices described in relation to FIGS. 4-7 above may also be suitable for the embodiment of FIG. 8.

In some embodiments, during delivery of therapeutic ultrasound, an MIT device 1506, such as described herein this section or elsewhere in the specification and applied such as described herein this section or elsewhere in the specification, may collect magnetic induction imaging data of the internal tissue site before, during, or after delivery of therapeutic ultrasound. As described above, MIT advantageously allows for deep tissue data and image collection. Such imaging data may then be transmitted to a controller or processor 1508 (hereinafter "controller"), the controller configured to amplify the image data using EVM according to any suitable methods described herein this section or elsewhere in the specification. The controller may then transmit the amplified image to a display 1510 to display the image, in real-time, before, or after delivery of therapeutic ultrasound. In some embodiments, the controller may transmit the image in unamplified form, simply conveying the MIT image and associated data such as disclosed herein this section or elsewhere in the specification.

In some embodiments, the controller 1508 may be configured to analyse the amplified image such as via any suitable method disclosed herein this section or elsewhere in the specification such as in FIGS. 4-7, to detect minute changes in the image. For example, as described above, the controller may detect minute changes in movement or color of the internal tissue. Such information on the minute changes in the amplified image may provide information regarding the effectiveness of the therapeutic ultrasound. Therefore, the controller may be configured to use the amplified pixel data to detect strengthening/healing/reattachment of the damaged tissue, such as by detecting a minute increase in density of certain soft and/or hard tissues that comprise the tissues of a mammalian joint. Further, the controller may be configured to use the amplified pixel data to identify changes in perfusion, increases in blood or other fluid flow to the damaged tissue and/or the migration of certain cells to the damaged tissue. Such detecting of minute changes in the healing of the tissue may be used to calculate a healing factor, which indicates the effectiveness of the therapeutic ultrasound induced healing.

In some embodiments, the controller 1508 may be configured to provide an alert, such as any alert described herein this section or elsewhere in the specification when the healing factor exceeds or falls below a threshold indicative of healing. This alert may be used by a caregiver to adjust the therapeutic ultrasound. In some embodiments, the alert may indicate the need to specifically adjust the therapeutic ultrasound such as by altering the frequency, amplitude, or general pulse frequency such as to intermittent or continuous. The threshold may be set by a caregiver or provided automatically based on previous patient information or by values found in the literature. In some embodiments, upon exceeding or falling below a threshold level for a healing factor, the controller may communicate with the ultrasound delivery device to automatically alter the parameters of the ultrasound delivery such as by raising or lowering the frequency or amplitude, and/or by altering a pulse/continuous delivery pattern of ultrasound.

In certain embodiments, the ultrasound delivery device and MIT device may be configured to coordinate via the controller. For example, the controller may be configured to only collect MIT image data while the ultrasound delivery device is operating. In some embodiments, the controller may alter the direction, timing or other parameters of the MIT device in response to changes in the therapeutic ultrasound.

In some embodiments, the computing systems described herein may include one or more computing devices, for example, a server, a laptop computer, a mobile device (for example, smart phone, smart watch, tablet, personal digital assistant), a kiosk, automobile console, or a media player, for example. In some embodiments, the computing devices may include one or more central processing units (CPUs), which may each include a conventional or proprietary microprocessor. Computing devices may further includes one or more memory, such as random access memory (RAM) for temporary storage of information, one or more read only memory (ROM) for permanent storage of information, and one or more mass storage devices, such as a hard drive, diskette, solid state drive, or optical media storage device. In certain embodiments, the processing device, cloud server, server or gateway device, may be implemented as a computing system. In one embodiment, the modules of the computing systems are connected to the computer using a standard based bus system. In different embodiments, the standard based bus system could be implemented in Peripheral Component Interconnect (PCI), Microchannel, Small Computer computing system Interface (SCSI), Industrial Standard Architecture (ISA) and Extended ISA (EISA) architectures, for example. In addition, the functionality provided for in the components and modules of the computing devices disclosed herein may be combined into fewer components and modules or further separated into additional components and modules.

The computing devices disclosed herein may be controlled and coordinated by operating system software, for example, iOS, Windows XP, Windows Vista, Windows 7, Windows 8, Windows 10, Windows Server, Embedded Windows, Unix, Linux, Ubuntu Linux, SunOS, Solaris, Blackberry OS, Android, raspberry Pi, Arduino, or other operating systems. In Macintosh systems, the operating system may be any available operating system, such as MAC OS X. In other embodiments, the computing device may be controlled by a proprietary operating system. Conventional operating systems control and schedule computer processes for execution, perform memory management, provide file system, networking, I/O services, and provide a user interface, such as a graphical user interface (GUI), among other things.

The computing devices disclosed herein may include one or more I/O interfaces and devices, for example, a touchpad or touchscreen, but could also include a keyboard, mouse, and printer. In one embodiment, the I/O interfaces and devices include one or more display devices (such as a touchscreen or monitor) that allow visual presentation of data to a user. More particularly, a display device may provide for the presentation of GUIs, application software data, and multimedia presentations, for example. The computing systems disclosed herein may also include one or more multimedia devices, such as cameras, speakers, video cards, graphics accelerators, and microphones, for example.

In general, the word "module," as used herein, refers to logic embodied in hardware or firmware, or to a collection of software instructions, possibly having entry and exit points, written in a programming language, such as, for example, Python, Java, Lua, C and/or C++. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software modules configured for execution on computing devices may be provided on a computer readable medium, such as a compact disc, digital video disc, flash drive, or any other tangible medium. Such software code may be stored, partially or fully, on a memory device of the executing computing device, for execution by the computing device. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The block diagrams disclosed herein may be implemented as modules. The modules described herein may be implemented as software modules, but may be represented in hardware or firmware. Generally, the modules described herein refer to logical modules that may be combined with other modules or divided into sub-modules despite their physical organization or storage.

Each of the processes, methods, and algorithms described in the preceding sections may be embodied in, and fully or partially automated by, code modules executed by one or more computer systems or computer processors comprising computer hardware. The code modules may be stored on any type of non-transitory computer-readable medium or computer storage device, such as hard drives, solid state memory, optical disc, and/or the like. The systems and modules may also be transmitted as generated data signals (for example, as part of a carrier wave or other analog or digital propagated signal) on a variety of computer-readable transmission mediums, including wireless-based and wired/cable-based mediums, and may take a variety of forms (for example, as part of a single or multiplexed analog signal, or as multiple discrete digital packets or frames). The processes and algorithms may be implemented partially or wholly in application-specific circuitry. The results of the disclosed processes and process steps may be stored, persistently or otherwise, in any type of non-transitory computer storage such as, for example, volatile or non-volatile storage.

All of the features disclosed in this specification (including any accompanying exhibits, claims, abstract and drawings), and/or all of the steps of any method or process so disclosed, may be combined in any combination, except combinations where at least some of such features and/or steps are mutually exclusive. The disclosure is not restricted to the details of any foregoing embodiments. The disclosure extends to any novel one, or any novel combination, of the features disclosed in this specification (including any accompanying claims, abstract and drawings), or to any novel one, or any novel combination, of the steps of any method or process so disclosed.

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the principles and features disclosed herein. Certain embodiments of the disclosure are encompassed in the claim set listed below or presented in the future.

What is claimed is:

1. A treatment system, comprising:
a visualization sensor configured to be positioned over a tissue site, the visualization sensor configured to collect magnetic induction tomography video data of the tissue site;
an output configured to provide a first alert; and
a controller in communication with both the visualization sensor and the output, the controller configured to:
amplify the video data by Eulerian video magnification;
determine a treatment parameter from the amplified video data, wherein the treatment parameter is derived from a red-delta value and changes in pulse motion indicative of blood flow to the tissue site;
cause the output to provide the first alert in response to determining that the treatment parameter differs from a threshold;
identify areas of skin tension in the tissue site from the amplified video data;
identify Langer's Lines in the tissue site from the identified areas of skin tension; and
identify an intended incision site and wherein the controller is configured to provide a second alert in response to determining that an intended incision site is not aligned with the Langer's Lines.

2. The treatment system of claim 1, wherein the threshold corresponds to a probability of occurrence of a pressure injury.

3. The treatment system of claim 1, wherein the controller is contained within a smartphone.

4. The treatment system of claim 1, wherein the visualization sensor is configured to communicate wirelessly with the controller.

5. The treatment system of claim 1, wherein the controller is configured to communicate wirelessly with the output.

6. The treatment system of claim 1, wherein the controller is configured to compare the treatment parameter to a plurality of thresholds.

7. The treatment system of claim 1, wherein the visualization sensor comprises an RGB detector.

8. The treatment system of claim 1, wherein the first or second alerts comprise an audible alarm.

9. The treatment system of claim 1, wherein the first or second alerts comprise a visual alarm.

10. The treatment system of claim 1, wherein the controller is configured to determine a tissue parameter by calculating the change in a red value between two or more frames of the video data.

11. The treatment system of claim 1, wherein the controller is configured to provide the first alert when the magnetic induction tomography video data exceeds a threshold.

12. A method of operating a treatment system comprising a visualization sensor and a controller, the method comprising:
by the visualization sensor positioned over a tissue site, collecting video data of the tissue site; and
by the controller:
amplifying the video data by Eulerian video magnification;
determining a treatment parameter from the amplified video data, wherein the treatment parameter is derived from a red-delta value and changes in pulse motion indicative of blood flow to the tissue site;
causing provision of an alert in response to determining that the treatment parameter differs from a threshold;
identifying areas of skin tension in the tissue site from the amplified video data;
identifying Langer's Lines in the tissue site from the identified areas of skin tension; and
identifying an intended incision site and providing an incision site alert in response to determining that an intended incision site is not aligned with the Langer's Lines, the incision site alert comprising an orientation and a position.

13. The method of claim 12, further comprising the controller mapping the Langer's Lines over the video data and displaying the Langer's Lines on a display.

14. A treatment system, comprising:
a visualization sensor configured to be positioned over a tissue site, the visualization sensor configured to collect video data of the tissue site;
an output configured to provide a first alert; and
a controller in communication with both the visualization sensor and the output, the controller configured to:
amplify the video data by Eulerian video magnification;
determine a treatment parameter from the amplified video data, wherein the treatment parameter is derived from a red-delta value and changes in pulse motion indicative of blood flow to the tissue site;
cause the output to provide the first alert in response to determining that the treatment parameter differs from a threshold;
identify areas of skin tension in the tissue site from the amplified video data;
identify Langer's Lines in the tissue site from the identified areas of skin tension;
identify an intended incision site and wherein the controller is configured to provide a second alert in response to determining that an intended incision site is not aligned with the Langer's Lines; and
map the Langer's Lines over the video data and display the Langer's Lines on a display.

* * * * *